(12) United States Patent
Schulz et al.

(10) Patent No.: US 10,646,505 B2
(45) Date of Patent: May 12, 2020

(54) DNA-FUNCTIONALIZED SCAFFOLDS FOR DRUG CAPTURE APPLICATIONS

(71) Applicant: CALIFORNIA INSTITUTE OF TECHNOLOGY, Pasadena, CA (US)

(72) Inventors: Michael D. Schulz, South Pasadena, CA (US); Carl M. Blumenfeld, Weston, FL (US); Robert H. Grubbs, South Pasadena, CA (US); Julia R. Greer, San Marino, CA (US); Daryl Wei Liang Yee, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/696,474

(22) Filed: Sep. 6, 2017

(65) Prior Publication Data

US 2018/0064747 A1 Mar. 8, 2018

Related U.S. Application Data

(60) Provisional application No. 62/384,625, filed on Sep. 7, 2016, provisional application No. 62/399,621, filed on Sep. 26, 2016.

(51) Int. Cl.

| A61K 31/711 | (2006.01) |
| C08F 222/10 | (2006.01) |
| A61L 29/08 | (2006.01) |
| A61L 31/16 | (2006.01) |
| A61L 29/16 | (2006.01) |
| A61K 47/58 | (2017.01) |
| A61K 47/69 | (2017.01) |
| A61K 47/54 | (2017.01) |
| A61L 31/08 | (2006.01) |
| A61L 31/10 | (2006.01) |
| A61L 31/14 | (2006.01) |
| C08F 293/00 | (2006.01) |

(52) U.S. Cl.
CPC .......... *A61K 31/711* (2013.01); *A61K 47/549* (2017.08); *A61K 47/58* (2017.08); *A61K 47/6923* (2017.08); *A61K 47/6929* (2017.08); *A61L 29/085* (2013.01); *A61L 29/16* (2013.01); *A61L 31/08* (2013.01); *A61L 31/10* (2013.01); *A61L 31/14* (2013.01); *A61L 31/16* (2013.01); *C08F 222/10* (2013.01); *C08F 293/005* (2013.01); *A61L 2300/258* (2013.01); *A61L 2400/12* (2013.01)

(58) Field of Classification Search
CPC ............................. A61K 31/711; C08F 222/01
See application file for complete search history.

(56) References Cited

U.S. PATENT DOCUMENTS

| 7,553,625 | B2 * | 6/2009 | Hoon ........................ B82Y 5/00 435/6.16 |
| 2009/0270593 | A1 * | 10/2009 | Bailey .................. C12Q 1/6825 530/350 |
| 2015/0361481 | A1 * | 12/2015 | Joun ..................... C12O 1/6846 506/26 |

FOREIGN PATENT DOCUMENTS

WO WO 2016/154345 * 9/2016

OTHER PUBLICATIONS

Pluim et al, Cytotoxicity of the organic ruthenium anticancer drug Nami-A is correlated with DNA binding in four different human tumor cell lines, 2004, 54, 71-78 (Year: 2004).*
Data sheet Idarubicin, Downloaded form National Center for Biotechnology Information. PubChem Compound Database; CID=42890, https://pubchem.ncbi.nlm.nih.gov/compound/42890 (accessed Feb. 26, 2019)., pp. 1-37 (Year: 2019).*
Bassik et al, Solvent Driven Motion of Lithographically Fabricated Gels, 2008, Langmuir, 24, 12158-12163. (Year: 2008).*
Livnah et al, Three-dimensional structures of avidin and the avidin-biotin complex, 1993, Proc. Natl. Acad. Sci. USA, 90, 5076-5080. (Year: 1993).*
Panda et al, Adsorption of organic molecules on silica surface, 2006, Advances in Colloid and Interface Science, 121, 77-110 (Year: 2006).*
Z. H. Siddik, Cisplatin: mode of cytotoxic action and molecular basis of resistance. Oncogene. 22, 7265-79 (2003).
Y. Song et al., Multimodal Gadolinium-Enriched DNA Gold Nanoparticle Conjugates for Cellular Imaging. Angew. Chem. Int. Ed. Engl. 48, 9143-9147 (2009).
X. C. Chen et al., Block Copolymer Membranes for Efficient Capture of a Chemotherapy Drug. ACS Macro Lett., 936-941 (2016).
S. J. Hurst et al., Synthetically programmable DNA binding domains in aggregates of DNA-functionalized gold nanoparticles. Small. 5, 2156-2161 (2009).
S. F. Altekruse, K. A. McGlynn, M. E Reichman, Hepatocellular carcinoma incidence, mortality, and survival trends in the United States from 1975 to 2005. J. Clin. Oncol. 27, 1485-1491 (2009).
R. P. Miller, R. K Tadagavadi, G. Ramesh, W. B. Reeves, Mechanisms of cisplatin nephrotoxicity. Toxins (Basel). 2, 2490-2518 (2010).
R. J. Macfarlane et al., Nanoparticle superlattice engineering with DNA. Science. 334, 204-8 (2011).
R. J. Lipshutz, S. P. Fodor, T. R. Gingeras, D. J. Lockhart, High density synthetic oligonucleotide arrays. Nat. Genet. 21, 20-4 (1999).
N. P. Tatonetti, P. P. Ye, R. Daneshjou, R. B. Altman, Sci TranslMed, in press, doi: 10.1126/scitranslmed. 3003377.
M. Ryberg et al., Epirubicin cardiotoxicity: An analysis of 469 patients with metastatic breast cancer. J. Clin. Oncol. 16, 3502-3508 (1998).
M. Beier, J. D. Hoheisel, Versatile derivatisation of solid support media for covalent bonding on DNA-microchips. Nucleic Acids Res. 27, 1970-1977 (1999).
L. Marelli et al., Transarterial therapy for hepatocellular carcinoma: Which technique is more effective? A systematic review of cohort and randomized studies. Cardiovasc. Intervent. Radiol. 30, 6-25 (2007).

(Continued)

Primary Examiner — Narayan K Bhat
(74) Attorney, Agent, or Firm — BakerHostetler

(57) ABSTRACT

This disclosure is directed to structured compositions, including DNA-functionalized scaffolds, for drug capture, and methods and devices for sequestering chemotherapeutics from physiological fluids using the functionalized scaffolds.

57 Claims, 18 Drawing Sheets

(56) References Cited

OTHER PUBLICATIONS

K. Shinozuka, Y. Seto, H. Kawata, H. Sawai, Bi-functional labelling of DNA with Iris (2-aminoethyl) amine-derived novel fluorescent agent. Bioorg. Med. Chem. Lett. 3, 2883-2886 (1993).
K. Cheung-Ong, G. Giaever, C. Nislow, DNA-Damaging Agents in Cancer Chemotherapy: Serendipity and Chemical Biology. Chem. Biol. 20, 648-659 (2013).
J. Belghiti, R. Kianmanesh, Surgical treatment of hepatocellular carcinoma. HPB (Oxford). 7, 42-49 (2005).
International Agency for Research on Cancer, World Cancer report 2008. Cancer Control. 199, 512 (2008).
H. Jo, C. Ban, Aptamer-nanoparticle complexes as powerful diagnostic and therapeutic tools. Exp. Mol. Med. 48, e230 (2016).
G. Yao etal., Clicking DNA to gold nanoparticles: poly-adenine-mediated formation of monovalent DNA-gold nanoparticle conjugates with nearly quantitative yield. NPG Asia Mater. 7, e159 (2015).
G. Minotti, P. Menna, E. Salvatorelli, G. Cairo, L. Gianni, Anthracyclines: molecular advances and pharmacologic developments in antitumor activity and cardiotoxicity. Pharmacol. Rev. 56, 185-229 (2004).
G. Cohen, J. Deutsch, J. Fineberg, A. Levine, Covalent attachment of hybridizable oligonucleotides to glass supports. Nucleic Acids Res. 25, 911-912 (1997).
E. T. H. Yeh, C. L. Bickford, Cardiovascular Complications of Cancer Therapy. J. Am. Coll. Cardiol. 53, 2231-2247 (2009).
E. D. Smolensky, K. L. Peterson, E. A. Weitz, C. Lewandowski, C. Pierre, Magnetoluminescent Light Switches—Dual Modality in DNA Detection Eric. J. Am. Chem. Soc.135, 8966-8972 (2013).
E. A. Tsochatzis, G. Germani, A. K. Burroughs, Transarterial Chemoembolization, Transarterial Chemotherapy, and Intra-arterial Chemotherapy for Hepatocellular Carcinoma Treatment. Semin. Oncol. 37, 89-93 (2010).
D. Wang, S. J. Lippard, Cellular processing of platinum anticancer drugs. Nat. Rev. Drug Deily. 4, 307-320 (2005).
D. Bovelli, G. Plataniotis, F. Roila, Cardiotoxicity of chemotherapeutic agents and radiotherapy-related heart disease: ESMO clinical practice guidelines. Ann. Oncol. 21, 277-282 (2010).
D. Agudelo, P. Bourassa, G. Berube, H. A. Tajmir-Riahi, Intercalation of antitumor drug doxorubicin and its analogue by DNA duplex: Structural features and biological implications. Int. J. Biol. Macromol. 66, 144-150 (2014).
D. Agudelo et al., Probing the binding sites of antibiotic drugs doxorubicin and N-(trifluoroacetyl) doxorubicin with human and bovine serum albumins. PLoS One. 7, 1-13 (2012).
C. S. Cleeland et al., Reducing the toxicity of cancer therapy: recognizing needs, taking action. Nat. Rev. Clin. Oncol. 9, 1-8 (2012).
C. A. Mirkin, R. L. Letsinger, R. C. Mucic, J. J. Storhoff, A DNA-based method for rationally assembling nanoparticles into macroscopic materials. Nature. 382 (1996), pp. 607-609.
A. U. Buzdar, C. Marcus, T. L. Smith, G. R. Blumenschein, Early and delayed clinical cardiotoxicity of doxorubicin. Cancer. 55, 2761-2765 (1985).
A. S. Patel etal., Development and Validation of Endovascular Chemotherapy Filter Device for Removing High-Dose Doxorubicin: Preclinical Study. J. Med. Device. 8, 0410081-0410088 (2014).
A. Polavarapu, J. A. Stillabower, S. G. W. Stubblefield, W. M. Taylor, M. H. Baik, The mechanism of guanine alkylation by nitrogen mustards: A computational study. J. Org. Chem. 77, 5914-5921 (2012).
A. M. Rahman, S. W. Yusuf, M. S. Ewer, Anthracycline-induced cardiotoxicity and the cardiac-sparing effect of liposomal formulation. Int. J. Nanomedicine. 2, 567-583 (2007).
A. Kumar, O. Larsson, D. Parodi, Z. Liang, Silanized nucleic acids: a general platform for DNA immobilization. Nucleic Acids Res. 28, E71 (2000).
He, et al., Communication; Aptamer based reversible DNA induced hydrogel system for molecular recognition and separation; 2010; 6308-6310.

* cited by examiner

FIG. 4B  FIG. 4C

HN3 method:

Cisplatin method:

DNA-FUNCTIONALIZED SCAFFOLDS FOR DRUG CAPTURE APPLICATIONS

CROSS REFERENCE TO RELATED APPLICATIONS

This application claims the benefit of priority from U.S. Patent Application Ser. No. 62/384,625, filed Sep. 7, 2016, and U.S. Patent Application Ser. No. 62/399,621, filed Sep. 26, 2016, the contents of which are both incorporated by reference herein for all purposes.

GOVERNMENT RIGHTS

This invention was made with government support under Grant No. CA194533 awarded by the National Institute of Health and under Grant No. DE-SC0006599 awarded by the Department of Energy. The government has certain rights in the invention.

TECHNICAL FIELD

This disclosure is directed to structured compositions, including DNA-functionalized scaffolds, for drug capture, and methods and devices for sequestering chemotherapeutics using the functionalized scaffolds.

BACKGROUND

The systemic toxicity of chemotherapy is a widely recognized problem in oncology. Off-target damage often persists indefinitely, adversely affects patient survival and compliance, and severely restricts dose and treatment options. Drug side effects remain a significant limitation for administration because of both expected and unexpected effects. Novel anticancer therapies have drastically improved life expectancy for numerous patients; however, persistent toxicity for long-term cancer survivors has become an issue, particularly for pediatric patients. In particular, cardiac toxicity may offset the increase in life expectancy resulting from the therapy due to mortality from cardiac problems including heart failure, myocardial ischemia, arrhythmias, hypertension, and thromboembolism.

Three common drugs used to treat cancers include doxorubicin (DOX), epirubicin (EPI), and cisplatin (FIG. 1), all of which act on DNA. DOX and EPI function by intercalating between DNA base pairs, while cisplatin is a DNA crosslinker that functions by binding to guanine. A major problem for these anticancer compounds is toxicity in non-targeted tissues. DOX and EPI toxicity can result in cardiomyopathy and congestive heart failure. Similarly, cisplatin exhibits side effects including extensive nephrotoxicity and neurotoxicity. Cumulative dosage of DOX is generally limited by clinicians to 400-450 mg/m$^2$, though lower cumulative dosages (300 mg/m$^2$) are known to increase the risk of congestive heart failure. Still, a single standard dose of DOX (50-75 mg) can result in severe side effects, while higher dosages of DOX are known to be associated with greater tumor suppression. Consequently, a balance must be struck in order to maximize the dose, leading to better tumor suppression, while simultaneously avoiding catastrophic off-target toxicity.

Limiting a patient's lifetime cumulative dose is the most effective way to avoid cardiotoxicity, but this approach necessarily limits anti-cancer efficacy.

The present invention(s) is intended to address some of these deficiencies.

SUMMARY

The present disclosure is directed to structured compositions comprising DNA linked to a surface of an organic or inorganic scaffold. Such structured compositions have several purposes, one of them being their use as instruments for removing drugs from physiological fluids. In such applications, additional embodiments include those where the structured compositions further comprise such a drug adhered to the linked DNA. In other independent embodiments, the structured compositions, with or without the adhered drug is in the presence of the physiological fluid.

In some embodiments, the DNA is or comprises genomic DNA. The DNA may also be or comprise synthetic DNA or other polynucleic nucleic acid.

In still other independent embodiments, the DNA is linked to the scaffold independently through one or more covalent linkages, and/or through one or more non-covalent linkages, for example comprising one or more linkages via intercalations, electrostatic, pi-pi, and/or hydrogen-bonding mechanisms.

The scaffolds may comprise an organic or inorganic material, either as a bulk material or as a coating on such a bulk material. Typically, the scaffold is insoluble or poorly soluble in a physiological or other aqueous medium, or is otherwise easily retrievable from such a medium.

The particular form of the scaffold is not limited, provided it allowed fluids to pass flow past, around, through, or over it. But it is highly preferred that the scaffold is of a form that a fluid is able to flow past, around, through, or over it with little flow resistance, especially when the structured composition is considered as material used to scrub drugs from the fluid. In certain embodiments, the scaffold is in the form of particles or beads, nanoparticles, microparticles, macroparticles, nanotubes, sheet surfaces, channels, tubes, nanofiber, microfiber, fibers, membranes, wires, meshes, webs, or other structures consistent with the ability to pass fluids through or around with facility.

The dimensions of these physical forms may range from the nanoscale to the millimeter scale, or larger. Again, in those applications contemplated for drug capture, exposed surface area is an important parameter, with larger surface area structures being preferred.

Where the scaffolds comprise or consist of organic polymers, such high surface area structures may comprise three-dimensional (3D) lattice structures. Such three-dimensional structures or features may be prepared by molding, spraying, or photochemical means, for example, by lithographic methods, such as are described elsewhere herein.

In preferred embodiments, the linkage(s) between the scaffold and the DNA are mainly or completely covalent in character, as such bonds tend to be more stable in use. The present disclosure contemplates all means for accomplishing such linkages. In defining the nature of such linkages between the scaffold and the DNA, it is convenient to describe means by which this linkage may be made. While the following descriptions are provided in terms of methods of making, it should appreciated that the corresponding structures are also considered independent embodiments of the disclosure. For example, in some embodiments, a functionalized scaffold, containing a linker, bonded to the scaffold, and presenting an electrophilic group (e.g., an aziridine or an alkyl group having a good leaving group) may be reacted with the nucleophilic moieties within DNA to form a linked scaffold-DNA moiety. Alternatively, a functionalized scaffold, containing a linker presenting a group capable of intercalating with a portion of the DNA molecule is so reacted with the DNA. In each case, the linked structure itself is an independent embodiment of this disclosure, as are the methods of making such structures.

The functionalized scaffold, containing a linker presenting an electrophilic group distal to the scaffold may be prepared directly, or by first preparing a nucleophilic surface on the scaffold, followed by reacting that nucleophilic surface with at least one linker group containing two or more separately reactive electrophiles. Any number of linker groups may be used, provided the final linker end distal from the scaffold is electrophilic.

For example, where the scaffold is or comprises a polymer, a functionalized scaffold may be prepared to present the electrophilic group directly by polymerizing or copolymerizing a composition comprising an unsaturated linker group having an electrophilic group (e.g., $H_2C=CH(CH_2)_n-X$, where X is a good leaving group). The system is chosen such that when polymerized, the electrophilic group is pendant (distal) to the surface of the scaffold. This may then be reacted with the DNA, to form the linked structure. The structured composition comprising the DNA-scaffold structure would be the result of this direct covalently linkage.

In another example, where the scaffold is or comprises a polymer, a electrophilically functionalized scaffold may also be prepared by first preparing a structure presenting a surface having reactive nucleophilic functional groups capable of further reaction with electrophilic linkers. In some embodiments, for example, the surface of the organic or inorganic scaffold may contain pendant hydroxide, thiol, amine, or carboxy acid moieties, suitable for reacting with linking moieties having at least one electrophilic end. Such materials may be prepared from polymer precursors containing such pendant moieties, for example vinyl alcohols, hydroxyalkyl (meth)acrylates or (meth)acrylamides, or glycerol (meth)acrylates or (meth)acrylamides. In specific embodiments, for example, the linkage to the scaffold may be accomplished starting from a hydroxylated surface polymer, which is then reacted with an electrophile, for example, a alkoxy-silane-containing linking moiety, the linker is or becomes covalently attached to the scaffold through a silyl ether (Si—O—C) linkage.

The same sort of strategy may be employed using substrates comprising inorganic (including metallic) surfaces, provided the surface is capable of such functionalization. In this regard, scaffold comprising hydroxylated inorganic materials can be functionalized as described herein (e.g., by acid etch or plasma treatment). Such hydroxylated inorganic materials may include clays, silicate glasses, metal alloys, or ceramic materials containing metal or metalloid hydroxy, oxide, or oxyhydroxide surfaces. In certain preferred embodiments, the linkages are attached to these surfaces using silyl ether linkages. In some of these embodiments, the metal or metalloid hydroxy, oxide, or oxyhydroxide surfaces may comprise Ag, Al, B, Ca, Cr, Fe, Mg, Ni, Si, Sn, Ti, Zn, or Zr. Other, more inert surfaces may also be contemplated, using suitable linking groups, for example, Au surfaces using thiol-based linkages.

Other embodiments of this disclosure include methods of removing drugs from physiological fluids, including blood and blood products using these inventive materials, and devices useful carrying out these methods. In certain specific embodiments, the methods remove drugs from patients to prevent systemic distribution of administered drugs throughout the patient's system.

Still other embodiments include those processes or methods for preparing the inventive structured compositions, including those structured compositions comprising scaffolds ranging from functionalized inorganic nanoparticles to three-dimensional photopolymerized polymers.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings:

FIG. 3A shows the decrease in DOX concentration in human serum, determined by fluorescence, as a result of DOX capture by IONP-HN3-DNA and IONP-Pt-DNA; 100±5 mg particle in 20 mL (0.05 mg/mL), 1 mg total DOX, 37° C.; error bars=1 standard deviation (n=3). FIG. 3B shows the decrease in DOX plasma concentration as a result of DOX capture by IONP-HN3-DNA from porcine whole blood; 100±5 mg IONP-HN3-DNA in 20 mL (0.05 mg/mL), 1 mg total DOX, 37° C.; error bars=1 standard deviation (n=3).).

FIG. 4B shows a brightfield image of IONP-HN3-DNA aggregates bound to doxorubicin. FIG. 4C illustrates the fluorescence from doxorubicin bound to IONP-HN3-DNA.

7C shows DOX concentration measurements from pre-device, mid-device, post-device, and peripheral locations.

Figure 8:
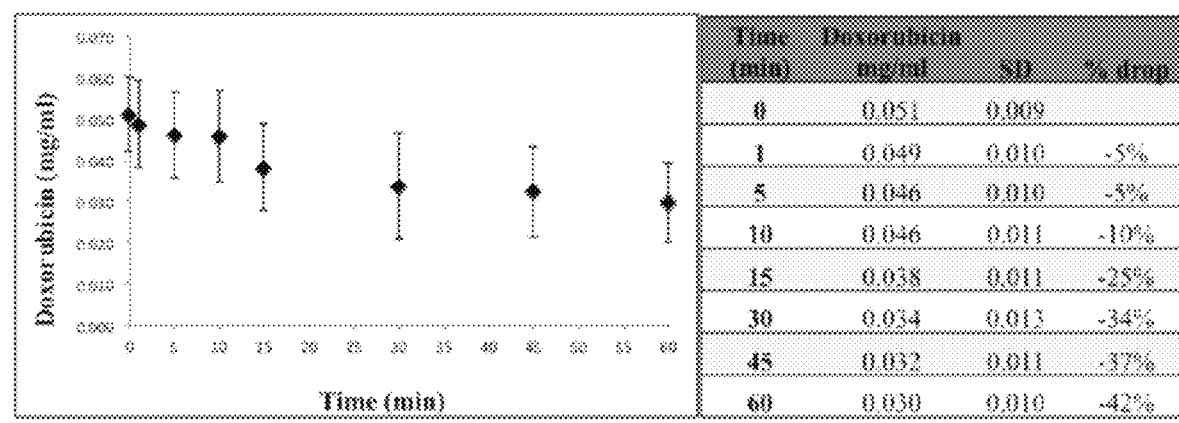

FIG. 8 shows doxorubicin clearance from porcine blood in closed loop flow 546 model.

Figure 9A:
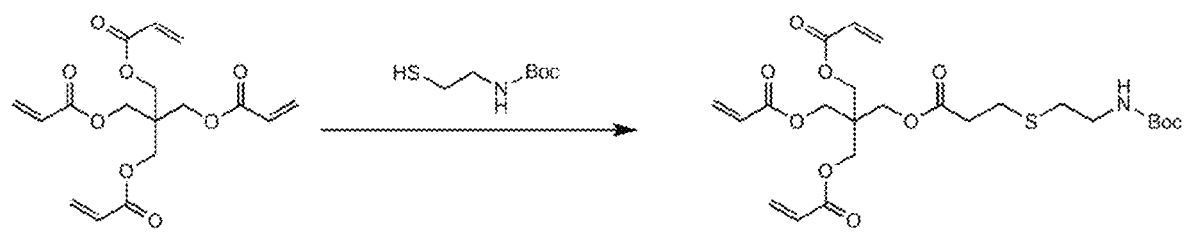
Figure 9B:
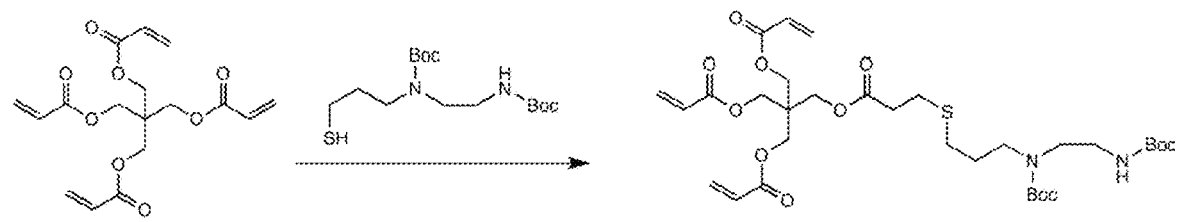
Figure 9C:
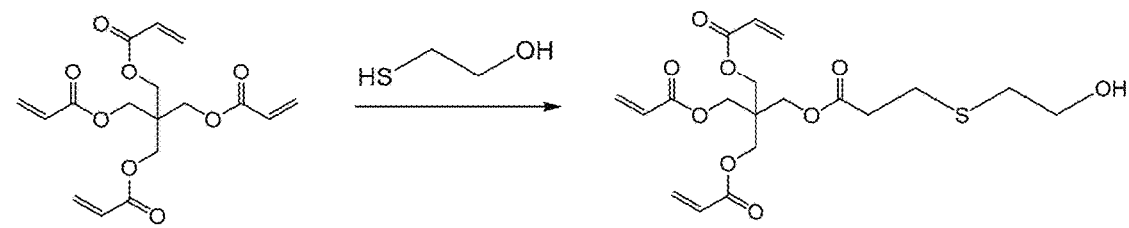

FIGS. 9A-C show schematic representation of exemplary embodiments for installing a Boc-protected amine or Boc-protected diamine or pendant alcohol onto the multifunctional acrylate via the thiol-Michael addition reaction. The molecules that can be used for this step are not limited to the ones shown above.

Figure 10:
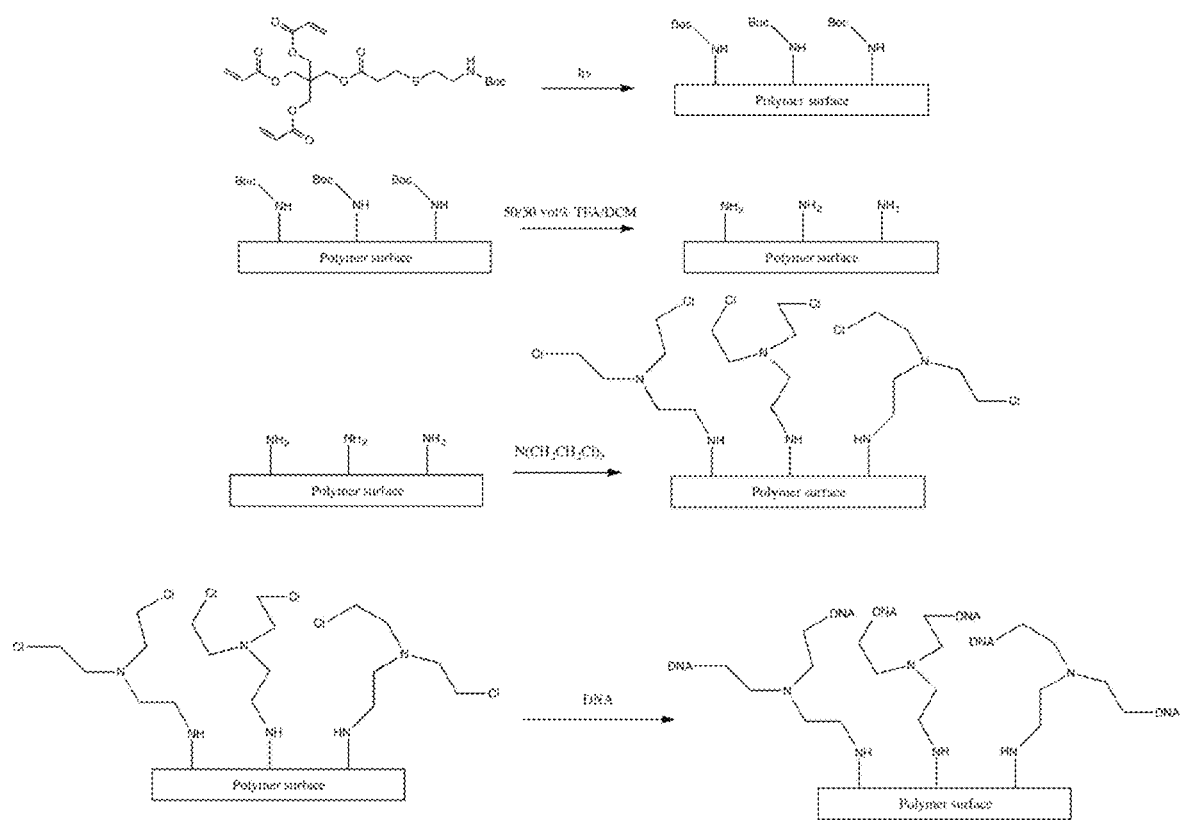

FIG. 10 shows one exemplary approach to covalently attaching genomic DNA via HN3. From top to bottom: 1) laser-induced photopolymerization of functionalized acrylate synthesized via the thiol-Michael addition. 2) Deprotection of the Boc-protected amines to primary amines. 3) Reaction of the primary amines with HN3. 4) Reaction of HN3 with genomic DNA.

Figure 11:
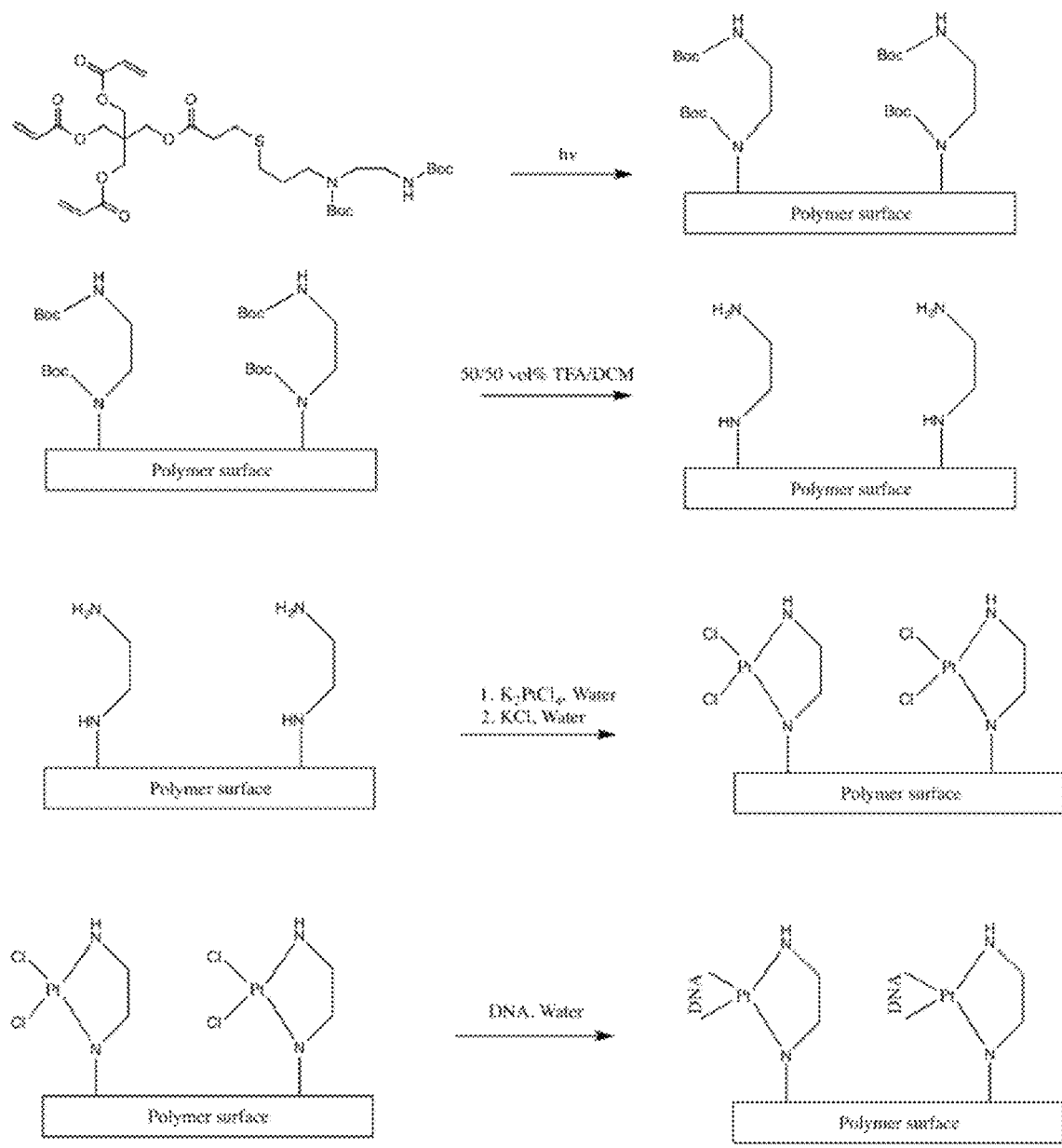

FIG. 11 shows another exemplary approach to covalently attaching genomic DNA via a cisplatin-like moiety. From top to bottom: 1) laser-induced photopolymerization of functionalized acrylate synthesized via the thiol-Michael addition. 2) Deprotection of the Boc-protected amines to amines. 3) Reaction of the amines with tetrachloroplatinate. 4) Reaction of the cisplatin analogue with genomic DNA.

Figure 12:
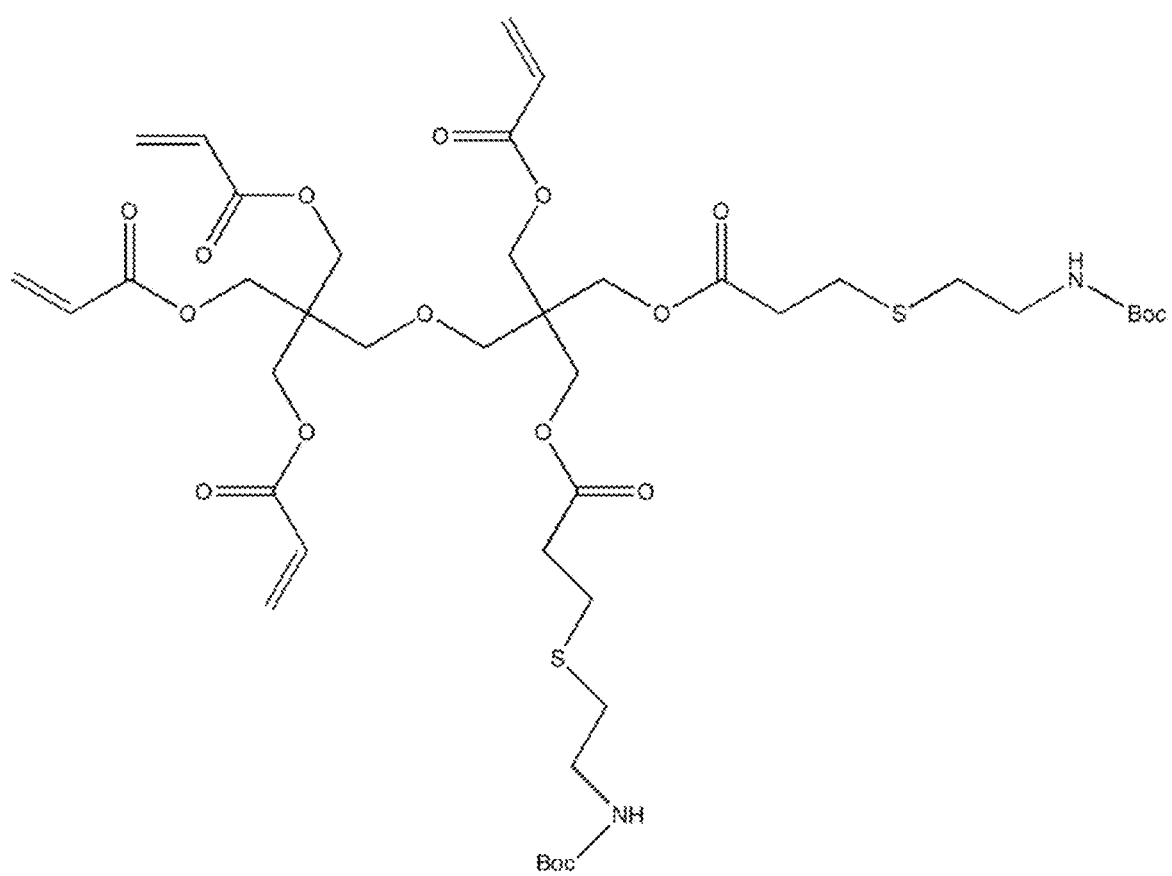

FIG. 12 shows a structural form of one of the products produced by reacting 2-(Boc-amino)ethanethiol and pentaerythritol tetraacrylate.

Figure 13:
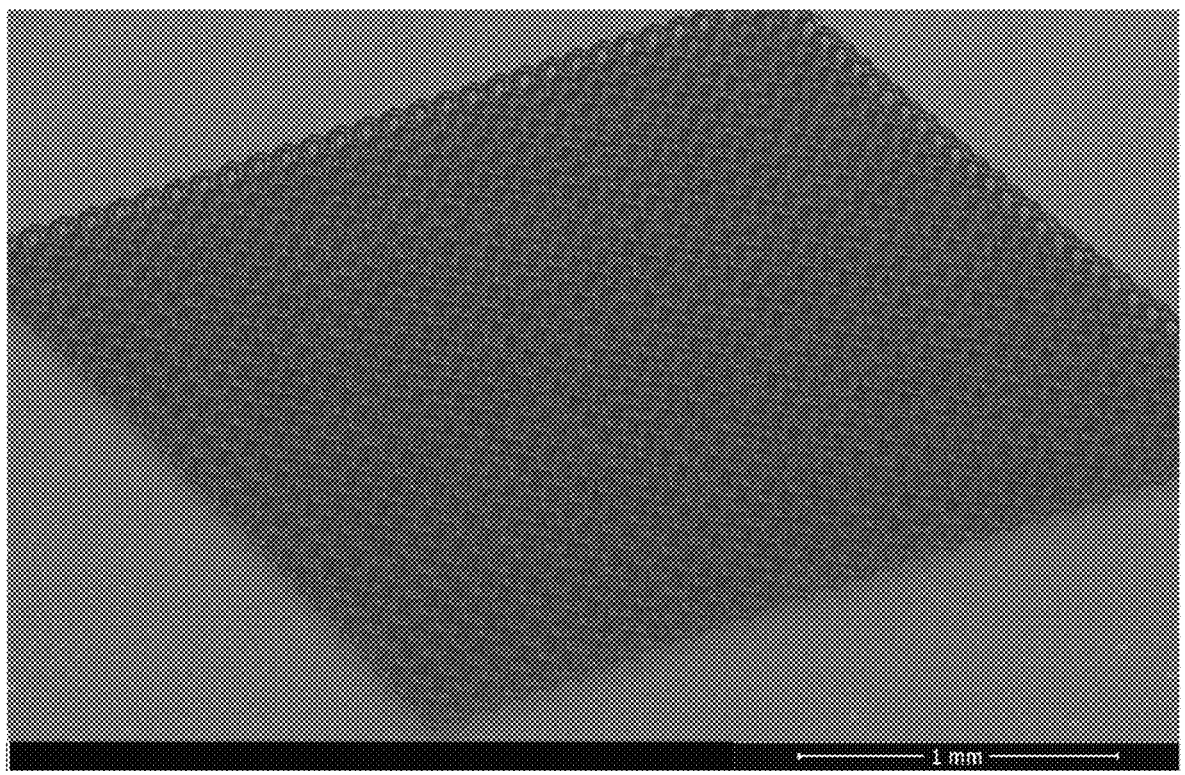

FIG. 13 shows an SEM image of a lattice created with two-photon lithography using the photoresist containing the functional monomer depicted in FIG. 12.

Figure 14:
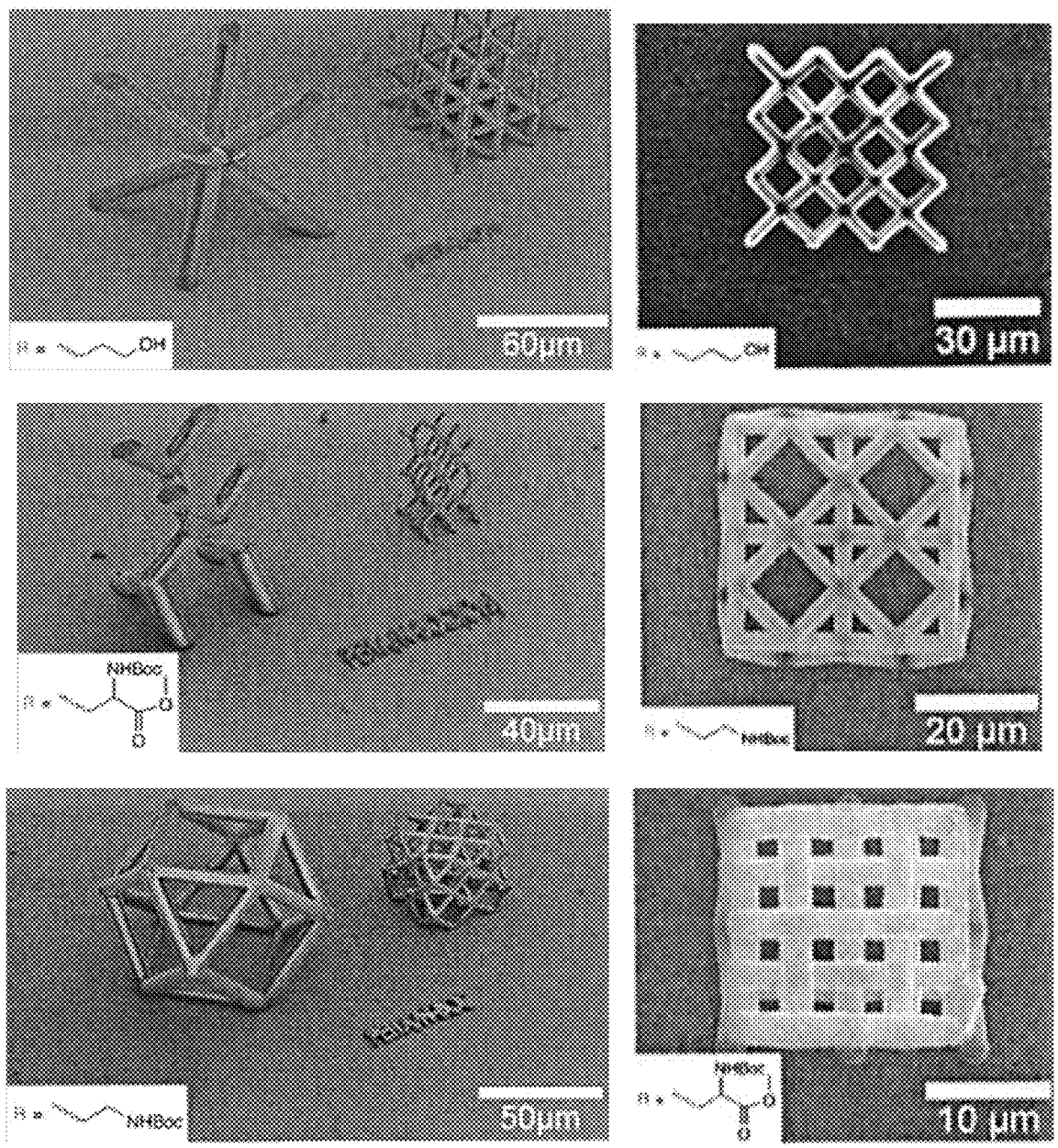

FIG. 14 shows other patterned organic scaffold structures available by the methods described in this disclosure.

Figure 15:
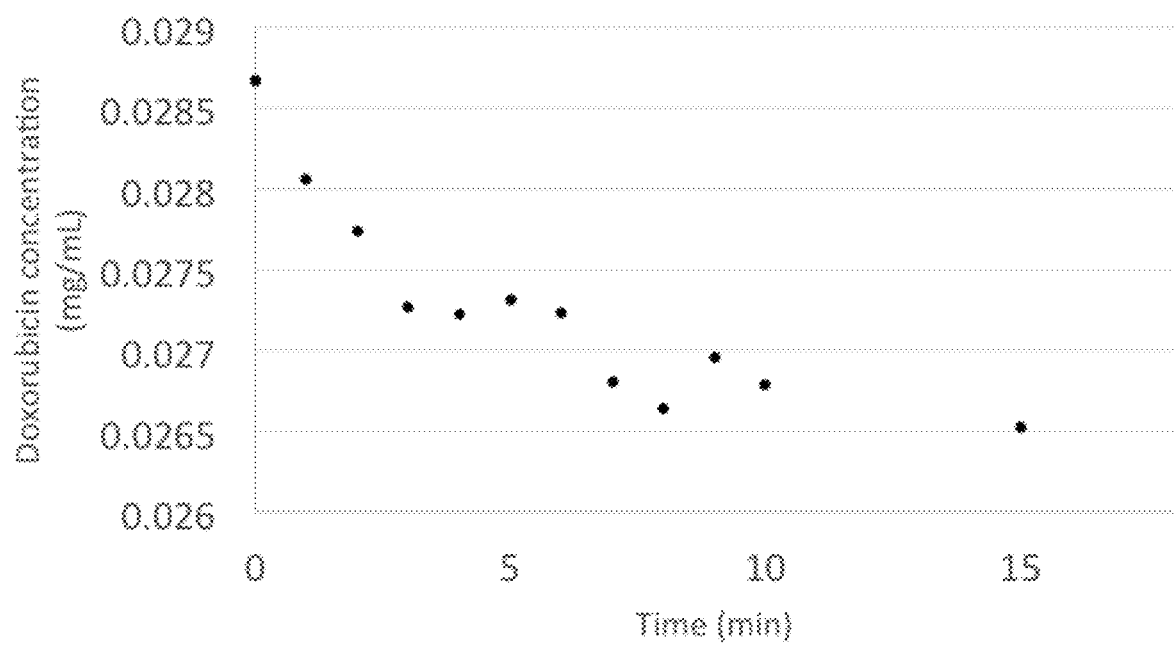

FIG. 15 shows the change in concentration of doxorubicin as a function of time. At t=0, the material was immersed in the solution. Approximately 10% of the doxorubicin in solution was bound to the material.

Figure 16A:
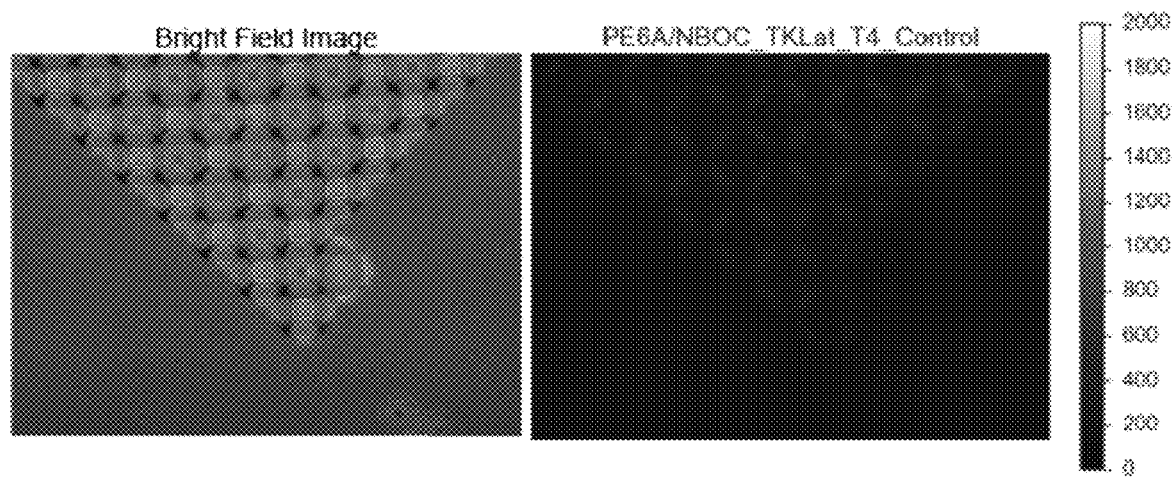
Figure 16B:
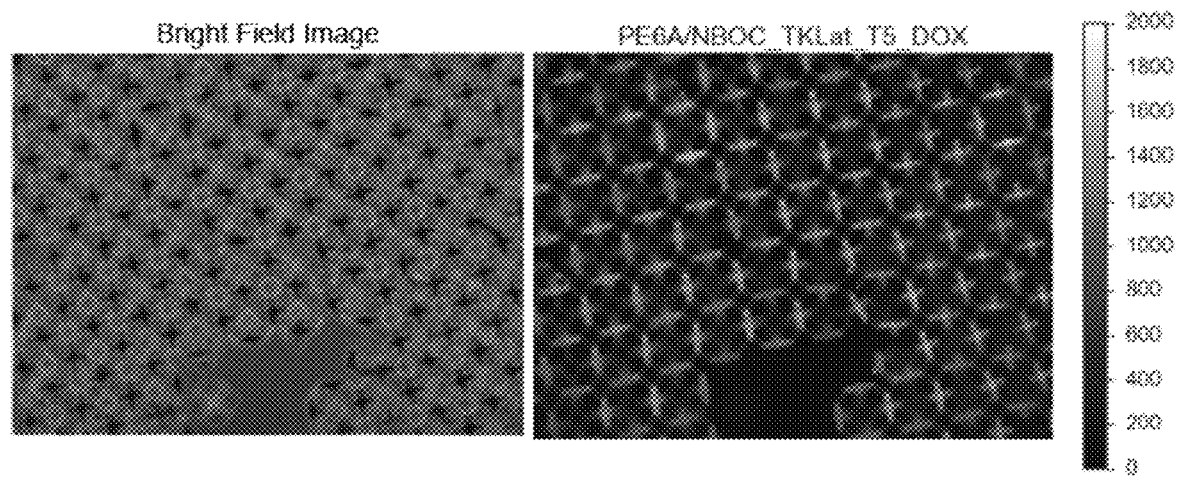

FIG. 16A shows a bright field (left) and fluorescence image (right) from the control. Some fluorescence could be seen from the auto-fluorescence of the photoinitiator. FIG. 16B shows a right field (left) and fluorescence image (right) from the material immersed in doxorubicin.

Figure 17:
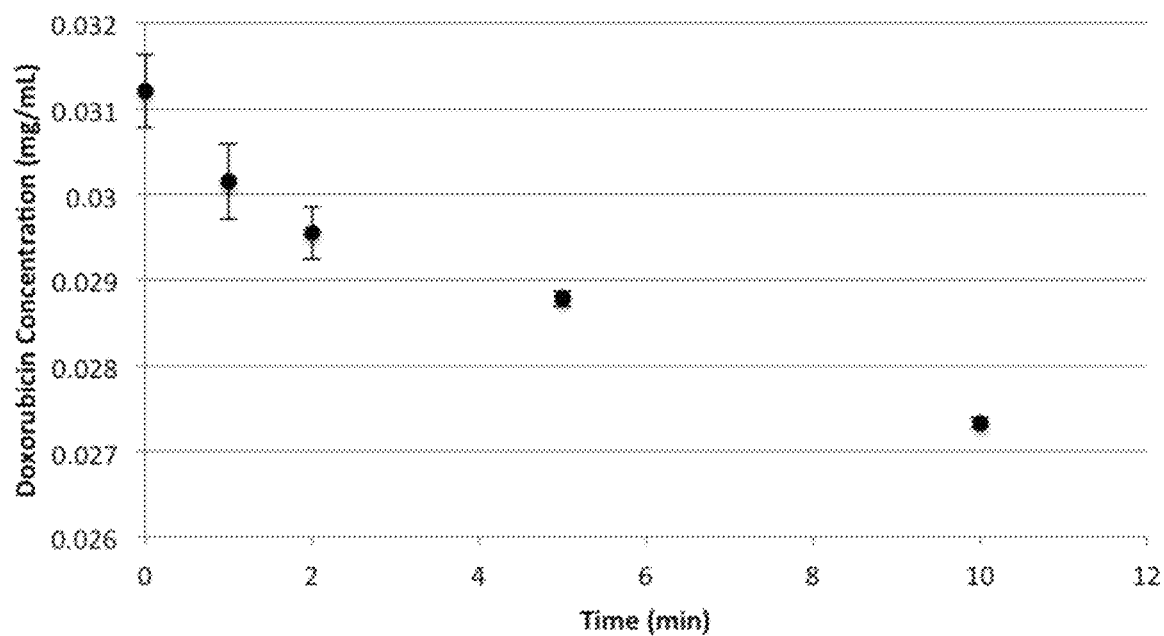

FIG. 17 shows the change in concentration of doxorubicin as a function of time. At t=0, the material was immersed in the solution. Approximately 12% of the doxorubicin in solution (0.039 mg) was bound to the material.

DETAILED DESCRIPTION OF ILLUSTRATIVE EMBODIMENTS

The present disclosure is directed to structured compositions comprising DNA operatively linked to a surface of an organic or inorganic scaffold. The disclosure further discloses devices derived from these structured compositions and methods of treating patients using these structured compositions and devices.

Still other embodiments include those processes or methods for preparing these inventive structured compositions, including those structured compositions comprising scaffolds ranging from functionalized inorganic nanoparticles to membranes to three-dimensional photopolymerized architected polymers.

Such structured compositions can serve several purposes, one of them being their use as instruments for removing drugs from physiological fluids, including blood or blood products, either in vitro or in vivo. In such applications, additional embodiments include those where the structured composition further comprises such a drug adhered to the linked DNA. In other independent embodiments, the structured compositions, with or without the adhered drug is in the presence of the physiological fluid. In some embodiments, the physiological fluid is blood or a blood product, e.g., blood plasma.

General Considerations

Certain embodiments of the present disclosure include those structured compositions comprising DNA operatively linked to a surface of an organic or inorganic scaffold. The term "operatively linked" refers to a chemical bonding linkage or chemically crosslinking mechanism. In separate independent embodiments, the DNA is operatively linked to the scaffold through one or more independent covalent linkages, and/or through one or more non-covalent linkages, for example comprising one or more linkages via intercalations, electrostatic, pi-pi, and/or hydrogen-bonding mechanisms. In preferred embodiments, the entire linking mechanism for the structured composition (scaffold to linkage to DNA) comprises covalent bonds. But there a number of mechanisms for binding the DNA to the functionalized scaffold that are sufficiently rigorous to fall within the scope of this disclosure. For example, and for the avoidance of doubt, the coordinative linkages associated with transition metal coordination chemistry (e.g., as in cis-platin derivatives) and the binding of such materials to DNA are deemed covalent linkages for the purposes of this disclosure. These and other mechanisms are described elsewhere herein.

The scaffolds may comprise one or more organic or inorganic material, either as a bulk material or as a coating on such a bulk material. For example, a metal, metalloid (e.g., Si), or ceramic coated with an inorganic oxide layer, a glass coated polymer, and a polymer coated glass scaffold are all non-limiting examples of scaffolds within the scope of this disclosure. Typically, the scaffold is insoluble or poorly soluble in a physiological or other aqueous medium, or is otherwise easily retrievable from such a medium. In some embodiments, the scaffolds are magnetic.

The particular form of the scaffold is not limiting or limited. But it is highly preferred that the scaffold be of a form that a fluid is able to flow past, around, through, or over the scaffold with little resistance or without significant pressure drop, especially when the structured composition is considered as material used to scrub drugs from the fluid. As used herein, "little resistance" or "without significant pressure drop" refers to a condition in which the build-up of pressure upon introduction of the structured compositions to a patient does not cause any adverse physiological effects in the patient. In certain embodiments, the scaffold is in the form of macroscopic or microscopic particles or beads, nanoparticles, nanotubes, optionally functionalized sheet surfaces, channels, tubes, tubules, nanofibers, microfibers, fibers, wires, membranes, meshes, webs, or other structures or combination thereof consistent with the ability to pass fluids through or around the structured compounds with facility. Particulate or fiber-based materials may be administered in porous mesh sacs that are or are not structured compositions. Two-dimensional flat, conformable, or curved sheet surfaces may also be optionally functionalized with three-dimensional features (e.g., channels, posts, through-holes) through or around which a fluid may pass. Fibers, microfiber, or nanofibers may be melt blown, spinneret spun, or electrospun. In such structures, the fibers, microfiber, or nanofibers themselves may be the scaffold compositions or the fibers may contain particulate materials that are the scaffold compositions. The webs or meshes may be woven or non-woven. The structures may be architected three-dimensional lattices, for example as derived from photochemical processing as described elsewhere herein. The scaffolds may comprise filled or unfilled membranes through which a fluid is directed to pass in use, with one or both surfaces and/or the filler materials functionalized as described elsewhere herein. Methods to prepare each of these physical forms, using the functionalized materials described herein are known in the art.

The scaffolds may comprise structures which are macroscopic, micro-dimensioned or nanodimensioned mesh, where micro-dimensioned and nano-dimensioned are defined as a form having at least one dimension in the range of from 1 to 1000 microns and 1 to 1000 nm, respectively. The term "macroscopic" is defined as having at least one dimensions larger than the other two, e.g., millimeter dimensioned. Again, in those applications contemplated for drug capture, exposed surface area is an important parameter, larger surface area structures being preferred. Where the scaffolds are in the form of particles or meshes, these materials can have BET surface areas in a range of from about 0.5 $m^2/g$ to about 100 $m^2/g$. In some embodiments these materials can have BET surface areas in a range of from about 0.5 to 1 $m^2/g$, from 1 to 5 $m^2/g$, from 5 to 10 $m^2/g$, from 10 to 25 $m^2/g$, from 25 to 50 $m^2/g$, from 50 to 100 $m^2/g$, or any combination of two or more of these ranges. In some embodiments, the BET surface areas are even higher.

Structured Compositions and Methods of Making the Structured Compositions Disclosed Herein General Concepts in Bonding to DNA Important to the approach described herein is the direct covalent attachment of DNA, including genomic DNA, to a scaffold. Up until now, functionalizing surfaces with DNA has mainly involved tagging either the backbone or bases of synthetic DNA with an appropriate functionality, or attaching the DNA via a reactive end-group. However, while such approaches are useful, by enabling complete control of the DNA sequence, they are limited in some ways by the relatively high cost of synthetic DNA. And while both synthetic and genomic DNA may be used in the structured compositions described herein, functionalization with genomic DNA is preferred as an alternative, cost-effective approach that may be appropriate for certain applications. The present inventors are unaware of any reports of the covalent attachment of genomic DNA to a nanoparticle, or any other scaffold surface.

As used herein, the term "DNA" refers to both genomic and synthetic DNA, though in separate independent embodiments, the DNA used in these structured compositions may independently either genomic or synthetic DNA or may comprise an RNA or other polynucleic acid having the ability to sequester drugs directly from flowing blood.

In independent embodiments, the DNA is linked to the linking group independently through one or more covalent linkages, and/or through one or more non-covalent linkages, for example one or more via intercalations, electrostatic, pi-pi, and/or hydrogen-bonding mechanisms. In separate independent embodiments, the DNA may be operatively linked to the scaffold/linker by covalent linkages, by coordination of the DNA to a pendant moiety attached to the linker, or by adsorption or anchoring using pendant intercalating groups. For avoidance of doubt, the coordinative linkages associated with Pt coordination chemistry (e.g., as in cis-platin derivatives) are deemed covalent linkages for the purposes of this disclosure. The covalent attachments of the DNA to the linker group may comprise an aliphatic or aromatic amide, amine, ester, ether, thioamide, thioester, or thioether bond. In specific embodiments, for example, the linkages to the DNA are derived from the in situ reaction of a pendant aziridinium moiety of a linker precursor. As described elsewhere herein, such bonds may result from the nucleophilic attack of nucleophilic moieties in the DNA structure with presented electrophilic groups provide in the pendant linker.

In defining the nature of the linkage between the scaffold and the DNA, it is also convenient to describe means by which this linkage may be made. For example, in some embodiments, a functionalized scaffold, containing a linker presenting an electrophilic group (e.g., an aziridine or an alkyl group having a good leaving group) may be reacted with the nucleophilic moieties within DNA to form a linked scaffold-DNA moiety. Alternatively, a functionalized scaffold, containing a linker presenting a group capable of intercalating with a portion of the DNA molecule. In each case, the linked structure itself is an independent embodiment of this disclosure, as are the methods of making such structures. The types of structures useful for presenting these electrophilic groups to the DNA and means for preparing them as discussed elsewhere herein.

The structured compositions may be used to captured or remove drugs from fluids, and as such, comprise operatively linked DNA, and so in further independent embodiments, DNA of the structured compositions may further comprise a captured drug, wherein the captured drug is bonded to the genomic DNA. As used herein, the term "captured" refers to the fact that the drug is covalently bonded, adsorbed, or otherwise reversibly or irreversibly attached to the DNA. These "captured" drugs may be bound by a binding motif that is the same or different from that used to anchor the DNA to the structured composite. Such captured drugs typically function by interacting with DNA in the body and can include, but are not limited to doxorubicin (DOX), epirubicin (EPI), daunorubicin, nitrogen mustards (such as bendamustine, chlorambucil, cyclophosphamide, ifosfamide, mechlorethamine, melphalan), nitrosoureas (such as carmustine, lomustine, streptozocin), alkyl sulfonates (such as busulfan), triazines (such as dacarbazine, temozolomide), ethylenimines (such as altretamine, thiotepa), trabectedin, or Pt-drugs (such as cisplatin, carboplatin, oxaliplatin).

Structured Compositions Comprising Organic Polymer Scaffolds, Including Three-Dimensional (3D) Structures As described elsewhere, the scaffolds may comprise or consist of organic materials, either as the bulk matrix or as a coating on another scaffold material. Practically any type of polymer may be employed for this purpose, provided that the surface of the structured composition presents functional groups capable of operatively linking DNA to the surface, either directly or via one or more intervening linking moieties. Such effects may be realized by judicious choice of polymers or copolymers incorporated into the structured composition, such that an appropriate functional group is presented for further reaction. As described elsewhere herein, certain moieties within DNA molecules have nucleophilic character, and are susceptible to reactions with electrophilic moieties, such that functionalizing the surface of the polymer with electrophilic moieties is useful in making such linkages with the DNA.

The functionalized scaffold, containing a linker presenting an electrophilic group distal to the scaffold may be prepared directly or by first preparing a nucleophilic surface on the scaffold, followed by reacting that nucleophilic surface with at least one linker group containing two or more separately reactive electrophiles. Any number of linkers may be used, provided the linker end distal from the scaffold is electrophilic.

For example, where the scaffold is or comprises a polymer, a functionalized scaffold may be prepared to present the electrophilic group directly by polymerizing or copolymerizing a composition comprising an unsaturated linker group having an electrophilic group (e.g., $H_2C=CH(CH_2)_n—X$, where X is a good leaving group). The system is chosen such that when polymerized, the electrophilic group is pendant (distal) to the surface of the scaffold. This may then be reacted with the DNA, for form the linked structure, and the structured composition would be the result of this direct covalently linked together.

In other embodiments, where the scaffold is or comprises a polymer, an electrophilically functionalized scaffold may also be prepared by first preparing a structure presenting a surface having reactive functional groups capable of further reaction with electrophilic linkers. In some embodiments, for example, the surface of the organic or inorganic scaffold may contain pendant hydroxide, thiol, amine, or carboxy acid moieties, suitable for reacting with linking moieties having at least one electrophilic end. Such materials may be prepared from polymer precursors containing such pendant moieties, for example vinyl alcohols, hydroxyalkyl(meth)acrylates or hydroxyalkyl(meth)acrylamides, or glycerol (meth)acrylates or glycerol(meth)acrylamides. Attractive polymeric or copolymeric building blocks include N-hydroxyalkyl acrylamide (where alkyl refers to $C_{1-6}$ alkyl), hydroxyalkyl(meth)acrylate, including 2-hydroxyethyl (meth)acrylate, 2-hydroxypropyl(meth)acrylate, 3-hydroxypropyl(meth)acrylate, 2-hydroxybutyl(meth)acrylate, 3-hydroxybutyl(meth)acrylate, and 4-hydroxybutyl(meth) acrylate, and glycerol mono(meth)acrylate, and poly(alpha-hydroxy acid).

The methods for providing the ultimate electrophilic moieties distal from the scaffold are wide and varied, including simple nucleophilic or electrophilic reactions, Michael additions, or click-chemistries (e.g., azide-alkyne). In some embodiment, as exemplified herein, polyolefins may be stoichiometrically functionalized with groups capable of adding to one or more of the olefins, providing one or more pendant groups that can then be further functionalized, as needed. See, e.g., FIGS. 9(A-C). In these methods, a thiolated compound containing either the Boc-protected amine or Boc-protected diamine can be reacted with a multifunctional polyunsaturated molecule. In some embodiments, the multifunctional polyunsaturated molecule is a multifunctional polyunsaturated acrylate monomer. Suitable multifunctional acrylate monomers include, but are not limited to, pentaerythritol triacrylate, pentaerythritol tetraacrylate, dipentaerythritol pentaacrylate and dipentaerythritol hexaacrylate. Suitable thiolated compounds include, but are not limited to 2-(Boc-amino)ethanethiol and tert-butyl (2-((tert-butoxycarbonyl)amino)ethyl)(3-mercaptopropyl)carbamate. In such a strategy, the degree of addition can be tuned by controlling the ratio of acrylate functional groups and the thiol functional groups. For example, a ratio of one mole of 2-(Boc-amino)ethanethiol to one mole of pentaerythritol tetraacrylate will give a product distribution with an average acrylate functionality of three, i.e. on average, each pentaerythritol tetraacrylate monomer would have reacted with one 2-(Boc-amino)ethanethiol molecule, and etc. In the examples shown in FIGS. 9(A-C), the tetraacrylate is functionalized to provide a nucleophilic pendant group (alcohol or protected amine) which requires additional functionalization to react with DNA. It is equally possible that the thiol linker group contain an electrophile (e.g., alkyl halide) instead of the hydroxy or protected amine, such that the resulting prepolymer is suitable for direct reaction with DNA.

Those structures providing exposed nucleophilic surfaces, for example hydroxylated, or other suitably functionalized surface having exposed thiol, amine, or carboxy acid moieties, may be reacted further with one or more difunctionalized linker groups, having either two electrophilic end groups or electrophilic and nucleophilic end groups, provided that the final linker provides the functionalized structure presenting the ultimate desired distal electrophilic group. The electrophilic end groups may include alkoxysilanes, epoxides, carboxylic acids or carboxylic halides (e.g., R—CO—Cl), organic halides, aziridines, and the like, and the nucleophilic end groups can include amines. Ultimately, linkers comprising alkoxysilane, ester, or ether linkages, which are substantially irreversibly bound when subjected to physiologically relevant conditions, are preferred. The final formed linkers should be stable in aqueous solutions, including physiological fluids such as described elsewhere herein. Preferably, the linkers should be hydrolytically stable under the uses contemplated (e.g., drug capture from blood or other physiological fluids), for example in a pH range of from 6.5 to about 8, preferably about 7 to about 7.5 (the normal pH of blood is tightly regulated in the body between 7.35 and 7.45). Representative functional linker groups and their corresponding linkers are exemplified herein.

Where the scaffolds comprise or consist of organic polymers, high surface area structures, such as microscopic or macroscopic particles or beads, nanoparticles, nanotubes, optionally functionalized sheet surfaces, channels, tubes, tubules, nanofibers, microfibers, fibers, wires, membranes, meshes, or webs, as described elsewhere herein. The use of organic polymers may also comprise three-dimensional (3D) lattice or other structures. Exemplary three-dimensional structures or features may be prepared by molding or photochemical means. For example, in certain embodiments, a pre-polymer material may be photopolymerized to form patterned structures. In some embodiments, the photopolymerization is done using two-photon lithography, 3D printing, micro-stereolithography and projection micro-stereolithography. Other multi-photon lithography methods may also be used, including interference lithography techniques such as phase mask lithography and proximity field nanopatterning. Other patterning strategies, including nanoimprint lithography, substrate conformal imprint lithography, stimulated emission and depletion lithography. The photosensitive compositions may be irradiated by any variety of methods known in the art. In certain embodiments, patterning may be achieved by photolithography, using a positive or negative image photomask. In other embodiments, patterning may be achieved by interference lithography (i.e., using a diffraction grating). In other embodiments, patterning may be achieved by proximity field nanopatterning. In still other embodiments, patterning may be achieved by diffraction gradient lithography. In still other embodiments, patterning may be used by a direct laser writing application of light, such as by multi-photon lithography. Additional embodiments provide that the patterning may be accomplished by nanoimprint lithography. Further, the patterning may be accomplished by inkjet 3D printing, stereolithography and the digital micromirror array variation of stereolithography (commonly referred to as digital light projection (DLP). These inventive structured compositions are especially amenable to preparing structures using stereolithographic methods, for example including digital light projection (DLP). "Stereolithography" is a method and apparatus for making solid objects by successively "printing" thin layers of a curable material, e.g., a UV curable material, one on top of the other. A programmed movable spot beam of UV light shining on a surface or layer of UV curable liquid is used to form a solid cross-section of the object at the surface of the liquid. The object is then moved, in a programmed manner, away from the liquid surface by the thickness of one layer, and the next cross-section is then formed and adhered to the immediately preceding layer defining the object. This process is continued until the entire object is formed. Such methods are summarized and described in U.S. Pat. No. 5,571,471, which is incorporated by reference herein in its entirety for its teaching of such methods.

The dimension of the features of such structures can be controlled, depending on the light source and conditions used to process the polymers. Certain exemplars of this technique are described in the Examples.

Conveniently, the functionalized scaffolds may be constructed with such architectures, followed by post-polymerization processing to attach the linker(s) and/or DNA to form the structured compositions. For example, in certain embodiments, the structured composition may be prepared by (a) photopolymerizing an appropriate precursor pre-polymer having an optionally protected pendant alcohol, amine, thiol, or carboxy acid, or other pendant moiety described herein to form a structured organic scaffold; removing the unpolymerized portion of the pre-polymer to form a featured structure;

(b) where the pendant moiety represented a protected moiety, deprotecting the optionally protected group to yield an unprotected alcohol, amine, thiol, or carboxy acid group or other reactive group;

(c) sequentially reacting this unprotected alcohol, amine, or carboxy acid group with one or more difunctionalized linker groups, each linker group having either two electrophilic end groups or electrophilic and nucleophilic end groups, so as to form a functionalized scaffold ultimately presenting an electrophilic group on the end of the linker distal to the functionalized scaffold; such an electrophilic group may be a alkoxysilane, alkyl halide, epoxide, or aziridine group, or is convertible to a pendant cis-platin-like moiety, to form a reactable scaffold; and (d) reacting the reactable scaffold with DNA under conditions to form a covalent linkage between the DNA and the linker.

In this embodiment, the electrophilic group suitable for binding to the DNA is applied post-polymerization. Still other embodiments provide that this group is provided in the monomer or oligomer pre-polymerization.

Structured Compositions Comprising Functionalized Inorganic Scaffolds

Inorganic materials also provide excellent scaffolds for use in these structured compositions. Such materials include metal, metalloids, and inorganic oxides, nitrides, and carbides, and alloys and composites derived from these materials.

And some of the strategies used for functionalizing organic substrates may also be employed using substrates comprising inorganic (including metallic) surfaces, provided the surface is capable of such functionalization. In this regard, inorganic scaffolds that may be functionalized for form the structured compositions may comprise hydroxylated, aminated, phosphorylated, or sulforylated inorganic materials. Such functionalized inorganic materials may include clays, silicate glasses, metal alloys (e.g., stainless steel, nitinol), or ceramic materials containing metal or metalloid hydroxy, oxide, or oxyhydroxide surfaces. Bulk metals, metal alloys, metalloids, nitrides, carbides, carbonitrides, oxynitrides, and oxycarbonitrides be surface-functionalized with known acid etch or plasma treatments to provide an appropriate functionalizable surface.

In independent embodiments, the inorganic materials comprise Li, Be, B, Na, Mg, Al, Si, P, K, Ca, Sc, Ti, V, Cr, Mn, Fe, Co, Ni, Cu, Zn, Ga, Ge, Rb, Sr, Y, Zr, Nb, Mo, Ru, Rh, Pd, Ag, Cd, In, Sn, Sb, Cs, Ba, Hf, Ta, W, Re, Os, Ir, Pt, and Au. These may be separately considered in Groups 1 to 15 of the Periodic Table. The inorganic scaffolds may be present as alloys, ceramics, glasses, and composites comprising one or more of these inorganic materials.

These inorganic materials may be in the form of macroscopic or microscopic particles or beads, nanoparticles, nanotubes, optionally functionalized sheet surfaces, channels, tubes, tubules, nanofibers, microfibers, fibers, wires, membranes, meshes, webs, or any other functional shapes.

In certain preferred embodiments, the metal or metalloids present surfaces comprising hydroxy, oxide, or hydroxyoxide groups. In some of these cases, the metal or metalloids which present these hydroxy, oxide, or oxyhydroxide surfaces may comprise Ag, Al, B, Ca, Cr, Fe, K, Mg, Na, Si, Sn, Ti, Zn, or Zr or any physiologically acceptable hydrous oxide with sufficient stability when functionalized under the contemplated application. Such functional groups allow for the functionalization of the surfaces as described elsewhere herein for organic polymer substrates. Other, more inert surfaces may also be contemplated using suitable linking groups. For example, Au or Ag surfaces may be functionalized using thiol-based linkages and Pt, Pd, and Ag surfaces may be functionalized with amine-based linkages. In the case of the inorganic particulate or fiber forms having hydroxy, oxide, or oxyhydroxide surfaces, bonding to linkers based on epoxide or silyl ether linkages, and especially silyl ether linkage, provide points of attachment sufficiently robust for use in contemplated applications, including chemotoxin scrubbing. Once functionalized, these inorganic scaffolds may be used to construct the structured compositions using any of the methods described elsewhere herein, including those for the structured organic compositions.

Conveniently, in certain embodiments, the structured inorganic composition may be prepared by:

(a) providing a surface comprising one or more hydroxy, oxy, oxyhydroxy, amine, thiol, or carboxy acid group to form a chemically reactive surface; this can be accomplished, for example, for non-oxides/non-sulfides using known plasma etching under oxidizing or nitriding conditions or wet chemical etching techniques;

(b) sequentially reacting this chemically reactive surface with one or more difunctionalized linker groups, each linker group having either two electrophilic end groups or electrophilic and nucleophilic end groups, so as to form a functionalized scaffold ultimately presenting an electrophilic group on the end of the linker distal to the functionalized scaffold; preferred groups for attaching such linker groups to the inorganic scaffolds include aminosiloxanes, though other electrophilic groups may be an alkyl halide, epoxide, or aziridine group, or is convertible to a pendant cis-platin-like moiety, to form a reactable scaffold; and (c) reacting the reactable scaffold with DNA under conditions to form a covalent linkage between the DNA and the linker.

Methods of Using the Structured Compositions

While several applications exist for these inventive structured compositions, including for example sensors, these compositions are especially attractive for use in removing chemotherapeutics and other drugs from physiological fluids, including saline and blood, and blood products (including serum and plasma) from mammalian patients. To be clear, certain embodiments provide methods of removing drugs, including chemotherapeutics, from a physiological fluid, the method comprising contacting the physiological fluid with any one or more of the structured composition described herein, for a time sufficient to remove at least a portion of the drug from the fluid. Exemplary drugs and fluids are described elsewhere herein. In preferred embodiments, the removal of the drug is done in vivo in a mammalian patient, especially a human patient, though it may be accomplished ex vivo using fluids previously extracted from the patient. Exemplary methods include trans- or intra-arterial infusion or chemotherapy or chemoembolization. In some embodiments, the methods allow for the local administration of chemotoxins into the body, for example, into a tumor or an organ, while at the same time preventing systemic distribution of administered drugs throughout the patient's system. In some embodiments, the structured compositions are positioned in the inferior vena cava, or in a vein exiting the liver, to prevent drugs injected into the liver from entering the body systemically. Such methods allow for the removal of off-target or after-use chemotherapeutics, but delivering the chemotherapy directly to a tumor via transarterial infusion, or similar procedures, and then sequestering any chemotherapeutic that enters systemic circulation.

Devices for Administering or Applying the Structured Compositions

In addition to methods of using these structured compositions, certain embodiments include those devices that can be used to administer these structured compositions in ex vivo and in vivo applications. Broadly speaking, such devices comprise a vessel containing the structured composition described herein, wherein the device is configured to allow a physiological fluid to flow through the device, while contacting the structured composition. For example, in some embodiments, the structured composition, in any one or more of the forms described herein, is placed within a vessel of the fluid containing the drug or drugs to be removed, with optional agitation (e.g., stirring or other mixing); after sufficient time for extraction (i.e., when sufficient amounts of the drugs are removed), the structured composition may be removed from the fluid. If particulate structured compositions are used, they can be removed by filtration, centrifugation, or other similar physical mode of separation. Particulate structured compositions can also be added to and retrieved from the fluid in porous sacs, these sacs being permeable to the fluids and drugs, but impermeable to the structured compositions. Structured compositions containing magnetic scaffolds can be removed by the application of a magnetic device. Membranes, webs, meshes, or latticed materials of sufficient size may simply be removed by hand or comparable methods; after sufficient time for extraction, the structured composition can be removed. The fluid within the vessel may be static or continuously exchanged with fresh (i.e., containing undepleted drugs) source fluid.

Alternatively, the physiological fluid may be brought to the structured compositions, either by tube, or similar device. For example, if the structured composition is of one of the particulate forms described herein, the composition may be contained in a stacked column, through which the fluid is passed, such that during the passage, the drugs are removed from the fluid by contact with the DNA of the structured composition. Similarly, such fluid may be directed to pass through membranes, webs, meshes, or lattices containing these structured compositions, the passage serving to provide the necessary contact for removal of the drug.

Expanding on these principles, other embodied devices include those capable of being inserted into a mammalian patient, in some cases, a human patient, such that the drug removal may be conducted in vivo. For example, in some embodiments, the structured composition is configured to be a medical device by itself, for example in the form of a functionalized solid fiber, membrane, web/mesh or hollow tubule, catheter, stent, or similarly structured form of sufficient size to be introduced in the circulatory or vascular system of a patient. In such cases, the structured composition is sufficiently strong to be used alone, without further support, as in the case of a metal wire or organic polymer fiber, microfiber, nanofiber. In such cases, the structured composition is sufficiently long and dimensioned to be insertible into the vein or artery of a patient. The elongated structured composition may also comprise a bristle-like appendages comprising the structured compositions, thus allowing the device to be able to form fit within the intended target artery or vein, thereby providing maximum contact between the flowing blood and the structured composition appendages.

In other embodiments, a structured fiber, wire, mesh, or membrane composition is deliverable to a position within a human patient through, or is incorporated into, a catheter, stent, cannula, or like flexible tubular device to be deliverable locally to a position within the patient. In such composite devices, the structured composition is configured to allow the structured fiber, wire, mesh, or membrane composition to be alternatively extendible from and retractable into the flexible tubular device. The structured composition may be of a form that is compressed when inside the catheter, stent, cannula, or like flexible tubular device, and is expanded when extended therefrom. Such compressibility may result from simple bristle-like configurations (e.g., like pipe cleaners) or may involve more complicated "umbrella-like" or "loop-type" construction (which open and close in extension/reinsertion; "loop-type" construction refers to one in which a flexibe wire forms an open loop with the membrane or mesh/web held within the area defined by the loop). Such configurations are known, albeit not in the present context of the inventive compositions. In preferred embodiments, the structured compositions, when expanded, fill the cross-sectional area of the blood vessel into which the catheter is to be or is inserted, while allowing facile passage of blood.

Where the medical devices comprise a catheter, stent, cannula, or like flexible tubular device, the device material may provide the scaffolding of the structured composition(s), in which case, the DNA is linked directly to the device material, or a coating (e.g., oxide or polymer) upon the device Terms In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the disclosure which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the disclosure that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of" and "consisting" are intended to connote their generally in accepted meanings in the patent vernacular. That is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention(s). Embodiments described in terms of the phrase "comprising" (or its equivalents), also provide, as embodiments, those that are independently described in terms of "consisting of" and "consisting essentially" of. For those embodiments provided in terms of "consisting essentially of," the basic and novel characteristic(s) is the operability of the methods (or the structured compositions or devices derived therefrom) as providing structures capable of removing drugs from physiological fluids without other means of doing so.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Throughout this specification, words are to be afforded their normal meaning, as would be understood by those skilled in the relevant art. However, to avoid misunderstanding, the meanings of certain terms will be specifically defined or clarified.

The term "substituted" as in "substituted alkyl," "substituted aryl," and the like, is meant to connote that in the hydrocarbyl, alkyl, aryl, heteroaryl, or other moiety, at least one hydrogen atom bound to a carbon (or other) atom is replaced with one or more non-hydrogen substituents. Examples of such substituents include, without limitation: functional groups referred to herein as "Fn," such as halo (e.g., F, Cl, Br, I), hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_1$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl ((CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)substituted carbamoyl (—(CO)—N($C_5$-$C_{24}$ aryl)$_2$), di-N—($C_1$-$C_{24}$ alkyl),N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)substituted thiocarbamoyl (—(CS)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl),N—($C_5$-$C_{24}$ aryl)-substituted thiocarbamoyl, carbamido (—NH—(CO)—NH$_2$), cyano (—C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)substituted amino, di-($C_5$-$C_{24}$ aryl)-substituted amino, $C_1$-$C_{24}$ alkylamido (—NH—(CO)-alkyl), $C_6$-$C_{24}$ arylamido (—NH—(CO)-aryl), imino (—CR═NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR═N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR═N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$OH), sulfonate (SO$_2$O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_1$-$C_{24}$ monoalkylaminosulfonyl-SO$_2$—N(H) alkyl), $C_1$-$C_{24}$ dialkylaminosulfonyl-SO$_2$—N(alkyl)$_2$, $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O)$_2$), phosphinato (P(O)(O—)), phospho (—PO$_2$), and phosphine (—PH$_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{24}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

Within these substituent structures, the "alkyl," "alkylene," "alkenyl," "alkenylene," "alkynyl," "alkynylene," "alkoxy," "aromatic," "aryl," "aryloxy," "alkaryl," and "aralkyl" moieties may be optionally fluorinated or perfluorinated. Additionally, reference to alcohols, aldehydes, amines, carboxylic acids, ketones, or other similarly reactive functional groups also includes their protected analogs. For example, reference to hydroxy or alcohol also includes those substituents wherein the hydroxy is protected by acetyl (Ac), benzoyl (Bz), benzyl (Bn, Bnl), β-Methoxyethoxymethyl ether (MEM), dimethoxytrityl, [bis-(4-methoxyphenyl)phenylmethyl] (DMT), methoxymethyl ether (MOM), methoxytrityl [(4-methoxyphenyl)diphenylmethyl, MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ether (most popular ones include trimethylsilyl (TMS), tert-butyldimethylsilyl (TBDMS), tri-iso-propylsilyloxymethyl (TOM), and triisopropylsilyl (TIPS) ethers), ethoxyethyl ethers (EE). Reference to amines also includes those substituents wherein the amine is protected by a BOC glycine, carbobenzyloxy (Cbz), p-methoxybenzyl carbonyl (Moz or MeOZ), tert-butyloxycarbonyl (BOC), 9-fluorenylmethyloxycarbonyl (FMOC), acetyl (Ac), benzoyl (Bz), benzyl (Bn), carbamate, p-methoxybenzyl (PMB), 3,4-dimethoxybenzyl (DMPM), p-methoxyphenyl (PMP), tosyl (Ts) group, or sulfonamide (Nosyl & Nps) group. Reference to substituent containing a carbonyl group also includes those substituents wherein the carbonyl is protected by an acetal or ketal, acylal, or diathane group. Reference to substituent containing a carboxylic acid or carboxylate group also includes those substituents wherein the carboxylic acid or carboxylate group is protected by its methyl ester, benzyl ester, tert-butyl ester, an ester of 2,6-disubstituted phenol (e.g. 2,6-dimethylphenol, 2,6-diisopropylphenol, 2,6-di-tert-butylphenol), a silyl ester, an orthoester, or an oxazoline. In each case, the protecting group may be attached and removed by standard methods known in the art.

By "functionalized" as in "functionalized hydrocarbyl," "functionalized alkyl," "functionalized olefin," "functionalized cyclic olefin," and the like, is meant that in the hydrocarbyl, alkyl, aryl, heteroaryl, olefin, cyclic olefin, or other moiety, at least one hydrogen atom bound to a carbon (or other) atom is replaced with one or more functional groups such as those described herein and above. The term "functional group" is meant to include any functional species that is suitable for the uses described herein. In particular, as used herein, a functional group would necessarily possess the ability to react with or bond to corresponding functional groups on a substrate surface.

The term "leaving group" is well understood in the field of organic chemistry, as a molecular fragment that departs from a carbon moiety with a pair of electrons in heterolytic bond cleavage. As used herein, the term "good leaving group" refers to chemical groups that include, but are not limited to halides (especially Cl—, Br—, and I—, perfluoroalkylsulfonates (e.g., triflate), sulfonate esters such as tosylate and mesitylates.

The terms "(meth)acrylate," "(meth)acrylamide," and the like refer to both acrylate and methacrylate components, each of which is considered an independent embodiment.

The terms "metal" and "metalloid" are intended to refer to materials other than organic polymers. Metals refer to elements, compounds, or alloys comprising one or more members of Groups 1 and 2 (alkali and alkaline earth metals), Groups 3 through 12 (transition metals) and some of Groups 13 through 15 (post-transition metals, including Ga, In, Sn, Pb, and Bi). As used herein, metalloids refer to non-conductive inorganic materials including aluminum, boron, silicon, germanium, arsenic, and antimony. These are typically present as their respective oxides, hydroxides, or oxyhydroxide in reference to the disclosed surface.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

As used herein, the term "genomic DNA" connotes the usual meaning understood by those skilled in the art. In certain interpretations, the term refers to chromosomal DNA, in contrast to extra-chromosomal DNAs like plasmids. The term may also be distinguished from "synthetic DNA," in that the latter refers to a natural or synthetic creation of DNA molecules, prepared, for example, by DNA replication (including DNA biosynthesis (in vivo DNA amplification)); polymerase chain reaction (including enzymatic DNA synthesis (in vitro DNA amplification)) and gene synthesis (including physically creating artificial gene sequences). In any case, reference to DNA includes, as independent embodiments, full and fragments of structures of the DNA.

The term "scaffold" refers to a physical structure linked to the DNA by optional organic or inorganic linkers. The structure may comprise a core comprising organic or inorganic (including metal and metalloid) materials, optionally coated by another organic or inorganic (including metal and metalloid) material which the same or different from the core material.

Additional Embodiments

The following listing of embodiments in intended to complement, rather than displace or supersede, the previous descriptions.

Embodiment 1

A structured composition comprising DNA operatively linked to a scaffold through an organic or inorganic surface of the scaffold, wherein the DNA is connected to the organic or inorganic surface by attachment to an intermediary linking group.

Embodiment 2

The structured composition of Embodiment 1, where the scaffold is in the form of a sheet, tube, microparticle, macroparticle, nanoparticle, nanotube, nanofiber, microfiber, fiber, wire, membrane, mesh, or web.

Embodiment 3

The structured composition of Embodiment 1 or 2, wherein the linking group comprises one or more internal covalent aliphatic or aromatic amide, amine, ester, ether, thioamide, thioester, or thioether bonds, or coordinative ligand linkages to a transition metal.

Embodiment 4

The structured composition of any one of Embodiments 1 to 3, wherein the DNA is genomic DNA.

Embodiment 5

The structured composition of any one of Embodiments 1 to 4, wherein the DNA is attached to the linking group by:
(a) a covalent aliphatic or aromatic amide, amine, ester, ether, thioamide, thioester, or thioether bond; or (b) intercalation or an electrostatic, pi-pi, and/or hydrogen-bonding mechanisms with a moiety on the linking group; or (c) bonding to a cis-platin-like moiety covalently attached to the linking group. Each of these bonding modes represents independent Embodiments.

Embodiment 6

The structured composition of any one of Embodiments 1 to 5, wherein the scaffold and/or the organic or inorganic surface comprises an organic polymer.

Embodiment 7

The structured composition of Embodiment 6, wherein the organic polymer contains a lithographically defined pattern.

Embodiment 8

The structured composition of any one of Embodiments 1 to 7, that comprises a three-dimensional (3D) architected polymer lattice.

Embodiment 9

The structured composition of any one of Embodiments 6 to 8, wherein the linking group is covalently bound to the organic polymer surface, the covalent bond resulting from the co-polymerization of an unsaturated moiety of a linker group precursor with a prepolymer of the organic polymer to form the linking group pendant to the surface.

Embodiment 10

The structured composition of any one of Embodiments 6 to 9, wherein the linking group is covalently bound to the organic polymer surface by chemical attachment to an otherwise hydroxylated organic polymer surface.

Embodiment 11

The structured composition of any one of Embodiments 6 to 10, wherein the linking group is covalently bound to the organic polymer surface by an aliphatic or aromatic amide, amine, ester, ether, thioamide, thioester, thioether or silyl ether linkage.

Embodiment 12

The structured composition of any one of Embodiments 6 to 11, wherein the organic polymer comprises a polyvinyl alcohol, a polyalkylhydroxy(meth)acrylate, a polyhydroxyalkyl(meth)acrylamide, a monoglycerol(meth)acrylate, a monoglycerol(meth)acrylamide or a combination thereof.

Embodiment 13

The structured composition of any one of Embodiments 6 to 11, wherein the organic polymer comprises (co)polymerized (meth)acrylate linkages.

Embodiment 14

The structured composition of any one of Embodiments 1 to 13, wherein the scaffold and the organic and/or inorganic surface comprises an inorganic metal or metalloid.

Embodiment 15

The structured composition of any one of Embodiments 1 to 14, wherein the scaffold and the organic and/or inorganic surface comprises an inorganic metal or metalloid oxide.

Embodiment 16

The structured composition of Embodiment 15, wherein the linking group is covalently bound to the inorganic surface by chemical attachment to an otherwise hydroxylated inorganic surface.

Embodiment 17

The structured composition of Embodiment 16, wherein the hydroxylated inorganic surface comprises a hydrous oxide of Al, B, Ca, Cr, Fe, Mg, Ni, Si, Sn, Ti, Zn, or Zr.

Embodiment 18

The structured composition of Embodiment 16 or 17, wherein the hydroxylated inorganic structured composition comprises a hydroxylated silicate glass or clay.

Embodiment 19

The structured composition of any one of Embodiments 16 to 18, wherein the linker group is covalently attached to the inorganic surface by a silyl ether linkage.

Embodiment 20

The structured composition of any one of Embodiments 1 to 19, further comprising a captured drug, wherein the captured drug is bonded or otherwise attached to the DNA.

Embodiment 21

The structured composition of Embodiment 20, wherein the captured drug comprises doxorubicin (DOX), epirubicin (EPI), daunorubicin, a nitrogen mustard, a nitrosourea, an alkyl sulfonate, a triazine, an ethylenimine, trabectedin, or a Pt-drug.

Embodiment 22

The structured composition any one of Embodiments 1 to 21 in physical contact with a physiological fluid.

Embodiment 23

The structured composition of Embodiment 22, wherein the physiological fluid is saline, blood, serum, or blood plasma.

Embodiment 24

A medical device comprising a structured composition of any one of Embodiments 1 to 23.

Embodiment 25

The medical device of Embodiment 24, wherein the structured composition is in a form of a structured fiber, wire, mesh, or membrane.

Embodiment 26

The medical device of Embodiment 25, wherein the structured composition is incorporated into a catheter, stent, cannula, or like flexible tubular device capable of being delivered locally to a position within the vascular system of a patient.

Embodiment 27

The medical device of Embodiment 26, constructed such that the structured composition is alternatively extendible from and retractable into the catheter, stent, cannula, or like flexible tubular device.

Embodiment 28

The medical device of any one of Embodiments 24 to 27, wherein the exterior surface of the catheter, stent, cannula, or like flexible tubular device is coated with a structured composition of claim 1.

Embodiment 29

A method of removing drugs from a physiological fluid, the method comprising contacting the physiological fluid with a structured composition of any one of Embodiments 1 to 23 for a time sufficient to remove at least a portion of the drug from the fluid. In certain Aspects of this Embodiment, the drugs are present at physiologically relevant concentrations, such as are discussed elsewhere herein. In other Aspects of this Embodiment, at least 10 wt %, 20 wt %, 30 wt %, 40 wt %, 50 wt %, 60 wt %, 70 wt %, 75 wt %, 80 wt %, 85 wt %, 90 wt %, or 95 wt % of the drug is removed from the fluid and captured by the DNA portion of the structured composition. In still other Aspects of this Embodiment, the method is conducted at physiologically relevant temperatures, for example, with 10° C., 5° C., or 3° C. of body temperature of the patient. In further Aspects of this Embodiment, the time sufficient represents an interval ranging from 1 to 5 minutes, from 5 to 10 minutes, from 10 to 15 minutes, from 15 to 20 minutes, from 20 to 25 minutes, from 25 to 30 minutes, from 30 to 40 minutes, from 40 to 60 minutes, or a combination of two or more of these intervals.

Embodiment 30

The method of Embodiment 29, wherein the method comprises trans- or intra-arterial chemotherapy. In some Aspects of this Embodiment, the method comprises transarterial chemoembolization.

EXAMPLES

The following Examples are provided to illustrate some of the concepts described within this disclosure. While each Example is considered to provide specific individual embodiments of structured composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Figure 1:
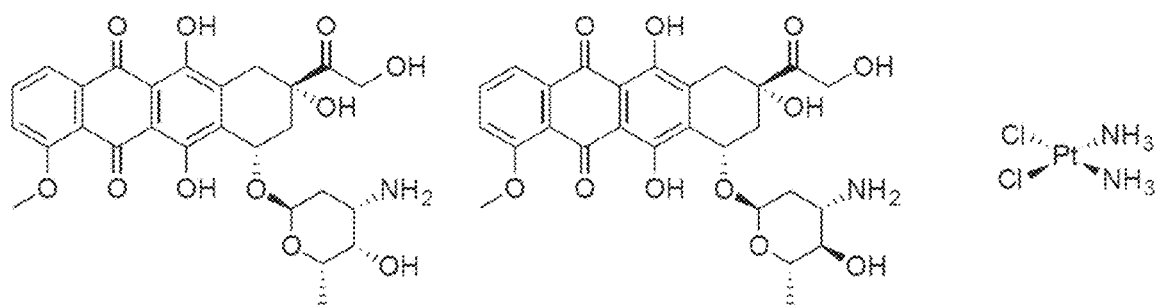
FIG. 1 show three commonly employed as chemotherapeutics: doxorubicin (DOX), epirubicin (EPI), and cisplatin.
Figure 2A:
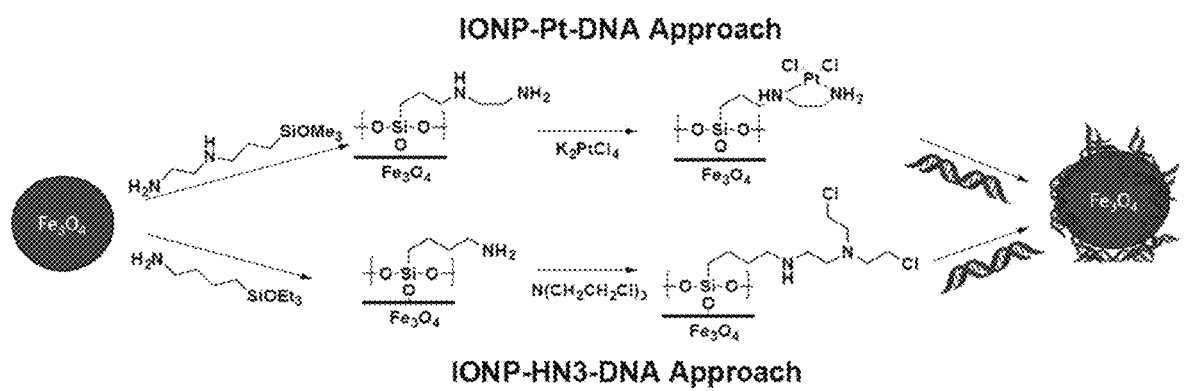
FIG. 2A shows two strategies for functionalizing hydroxylated substrates, as exemplified by hydrous iron oxide.
Figure 2B:
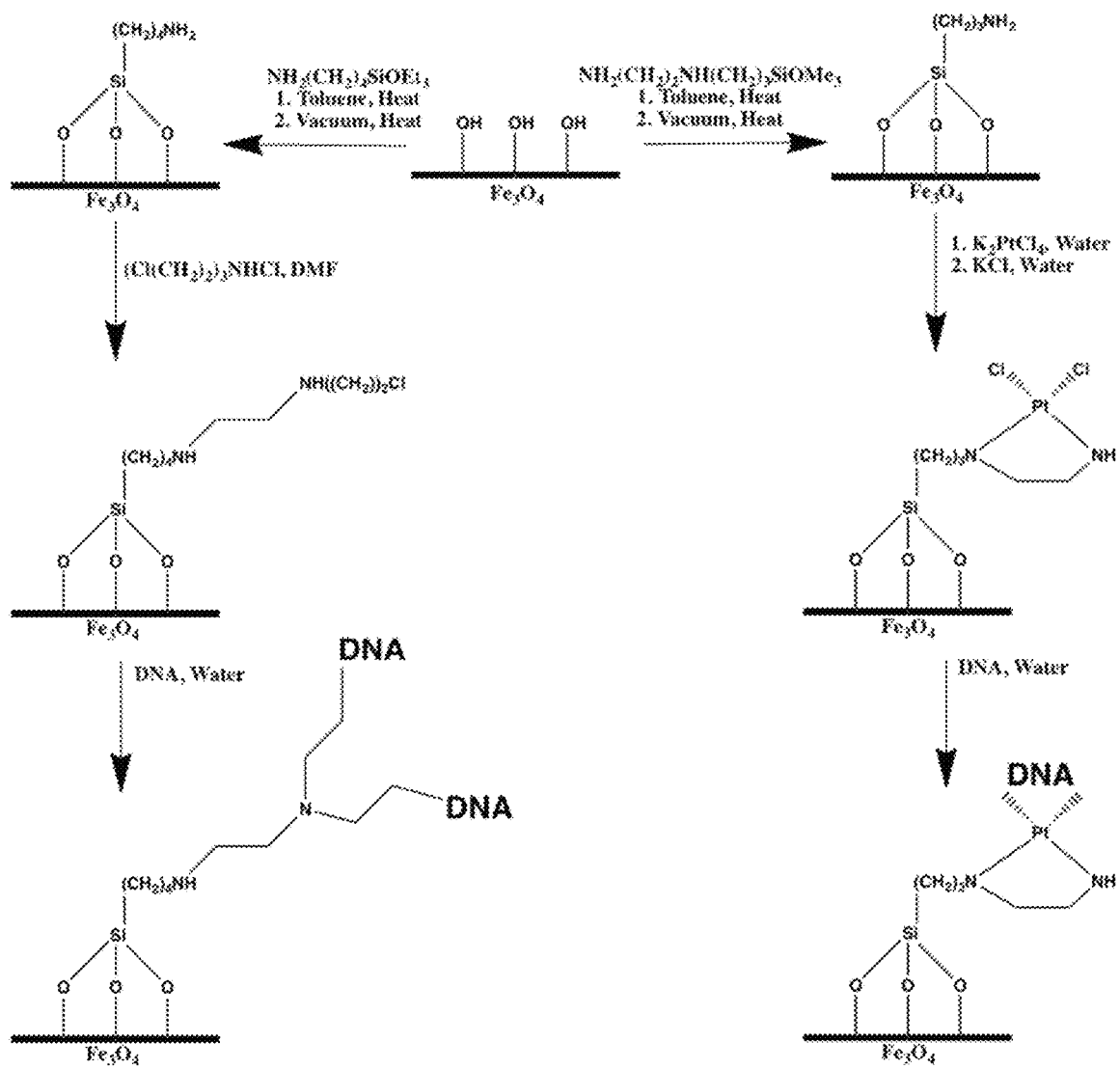
FIG. 2B shows expanded synthetic approach to magnetic scaffolds.
Figure 2C:
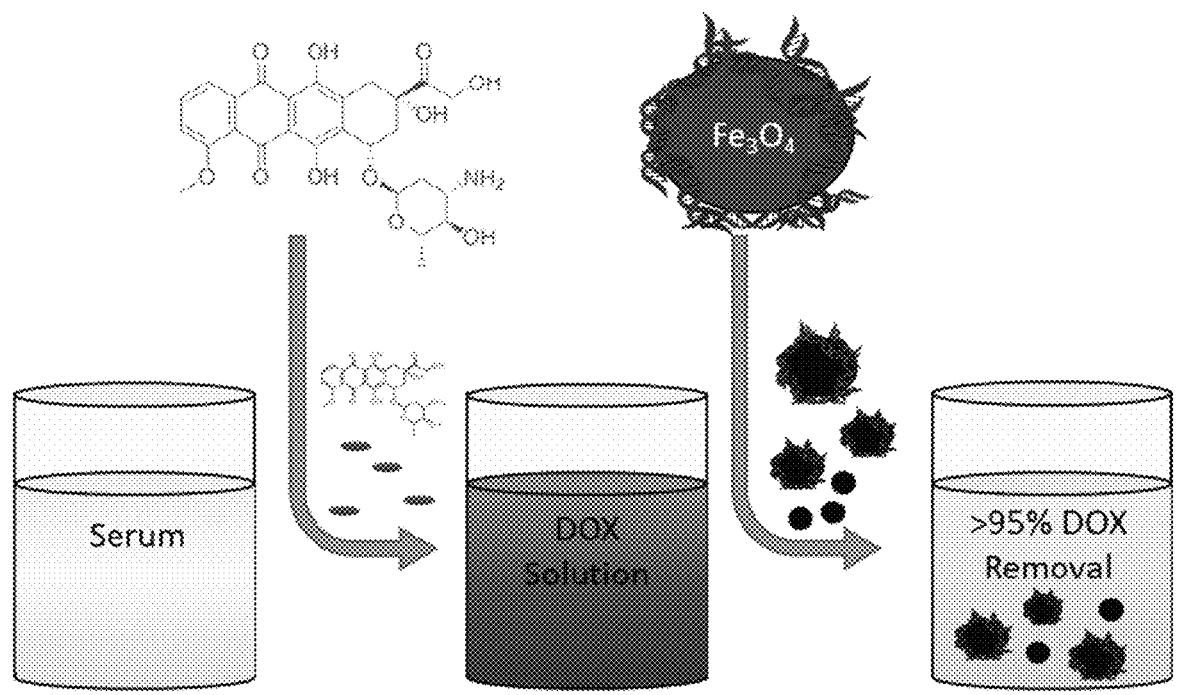
FIG. 2C shows a cartoon representation of one exemplary method of removing drugs from physiological fluids.

Herein are reported two methods, both demonstrated on multi-gram scale, of attaching DNA to particles (FIG. 2A), based on known DNA-crosslinking agents. The resulting materials are capable of removing DNA-targeting chemotherapy agents from solution both rapidly, and in the presence of potential biological interferants (e.g., serum proteins).

While the inorganic exemplars describe herein focus on iron oxide, specifically magnetite, the principles disclosures are generally applicable to a wider range of materials. With these structured compositions, three common chemotherapy agents—doxorubicin, cisplatin, and epirubicin—were captured from biological solutions at remarkable efficiencies. Greater than >80% capture of doxorubicin was achieved from human serum in 1 minute, with 98% capture in 10 minutes, all at physiologically relevant concentrations. Finally, the in vivo efficacy of these materials was demonstrated in a porcine model, which showed an 82% reduction in doxorubicin concentration over the length of a particle-coated device. The efficacy of these materials indicates that drug capture is a viable strategy for mitigating chemotherapy-associated side effects.

Example 1

DNA-alkylating agents are a common motif in chemotherapy. By forming covalent crosslinks between DNA strands, these drugs prevent the DNA from being accurately duplicated, ultimately leading to apoptosis. To attach genomic DNA to magnetic particles, the present inventors used an approach analogous to DNA-alkylating/crosslinking drugs (FIG. 2A), though other analogous agents are contemplated within the scope of this disclosure.

Example 1.1

A first approach was inspired by cisplatin. To synthesize IONP-Pt-DNA samples (IONP=iron oxide nanoparticles), the hydroxylated surface of magnetite was silylated with N-(2-aminoethyl)-3-aminopropyltrimethoxysilane to expose a chelating diamine functionality. This sample was treated with an excess of potassium tetrachloroplatinate under aqueous conditions to create an analogue to cisplatin by which DNA could be anchored on the surface. Cisplatin's cytotoxicity is thought to stem from its coordination with nucleophilic N7-sites of purine bases, resulting in crosslinks, and this mechanism formed the intended basis for the instant methods. The sample was then exposed to DNA to afford IONP-Pt-DNA.

Example 1.2

A second approach was modeled on nitrogen mustard chemotherapy agents. IONP-HN3-DNA samples were prepared first by functionalizing magnetite with 4-aminobutyltriethoxysilane to install free amine on the surface. This particle was then treated with excess tris(2-chloroethyl)amine hydrochloride to create a scaffold for DNA functionalization. Tris(2-chloroethyl)amine hydrochloride, the hydrochloride salt of the nitrogen mustard, HN3, when deprotonated, can undergo aziridinium formation, which is attacked readily by the nucleophilic moieties of DNA. The functionalized particle was exposed to DNA resulting in IONP-HN3-DNA. Both materials were characterized by scanning electron microscopy, electron dispersive scattering, elemental analysis, and infrared spectroscopy (see Supplementary Information).

Example 1.3. Solution Testing

In order to evaluate the efficacy of these scaffolds at scavenging chemotherapy agents from solution, the DNA-coated particles (IONP-Pt-DNA) were tested in PBS solution containing a physiologically relevant concentration of DOX (0.05 mg/mL). DOX was selected not only because it is one of the most commonly used chemotherapy agents, but also because its fluorescence emission enables simple quantification of concentration in solution. Initial experiments were performed using 20 mL of 0.05 mg/mL DOX solution and 35 mg of particles. This amount of particle was chosen to ensure that the amount of DOX was much larger than the amount of DNA, leading to saturation of the scaffold. Rapid kinetics were observed, with over 20% of the total amount of DOX absorption occurring within one minute. Despite DOX being in large excess compared to the total amount of DNA in the system, over 40% (0.4 mg) of the drug was removed from solution within 25 minutes.

A similar experiment was conducted to investigate DOX-binding in human serum at 37° C., in order to approximate the biological environment in which these materials would have to operate. Interestingly, the efficacy of the scaffolds was virtually unchanged, despite the known binding of DOX with serum albumin. It appears that intercalation with DNA is a kinetically favorable process, and that this kinetic advantage enabled these materials to capture DOX from serum solution, despite the thermodynamics being overall in favor of serum binding. It may be that over longer timescales, serum binding would be the dominant process; however, since TACE is a relatively short procedure (<1 h), it is expected that kinetic factors will dominate in the performance of any material or device.

Figure 3A:
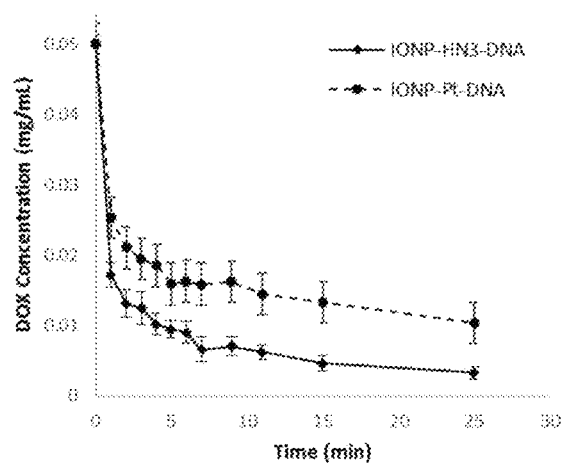
FIGS. 3A-B show the results described in Example 1.3.

To confirm that both synthetic approaches to DNA-based scaffolds produced effective materials and to compare their efficacy, DOX-capture studies were performed in human serum. IONP-HN3-DNA was found to be able to capture 93% of DOX, on average, from a 0.05 mg/mL solution in 25 minutes, while IONP-Pt-DNA averaged 79% (FIG. 3A). In both cases, the kinetics were extremely rapid, with about 50% of DOX capture occurring within one minute in the case of IONP-Pt-DNA and over 65% DOX capture occurring within one minute for IONP-HN3-DNA. Based on these results, all further tests were carried out with IONPHN3-DNA.

Figure 3B:
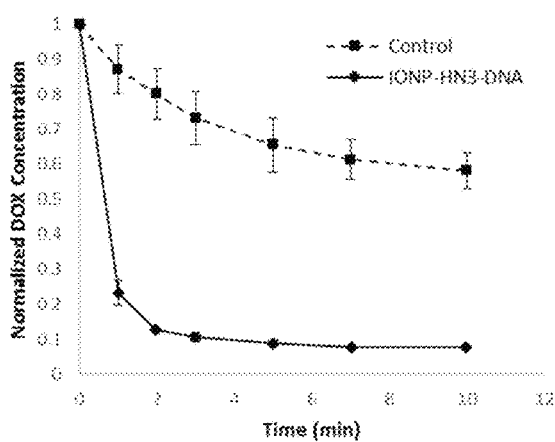

Drug capture was also evaluated in porcine whole blood, by measuring DOX plasma concentration over time. Some DOX removal was observed due to binding to the non-plasma blood components, which could not be deconvoluted from capture by these materials. Nevertheless, there is rapid reduction of DOX concentration in the blood plasma within 1 minute after exposure to these materials, reaching a 92% reduction in DOX plasma concentration over 10 minutes, in stark contrast to the control experiment (FIG. 3B). This experiment conclusively demonstrates that these materials are capable of capturing DOX from whole blood.

Figure 4A:
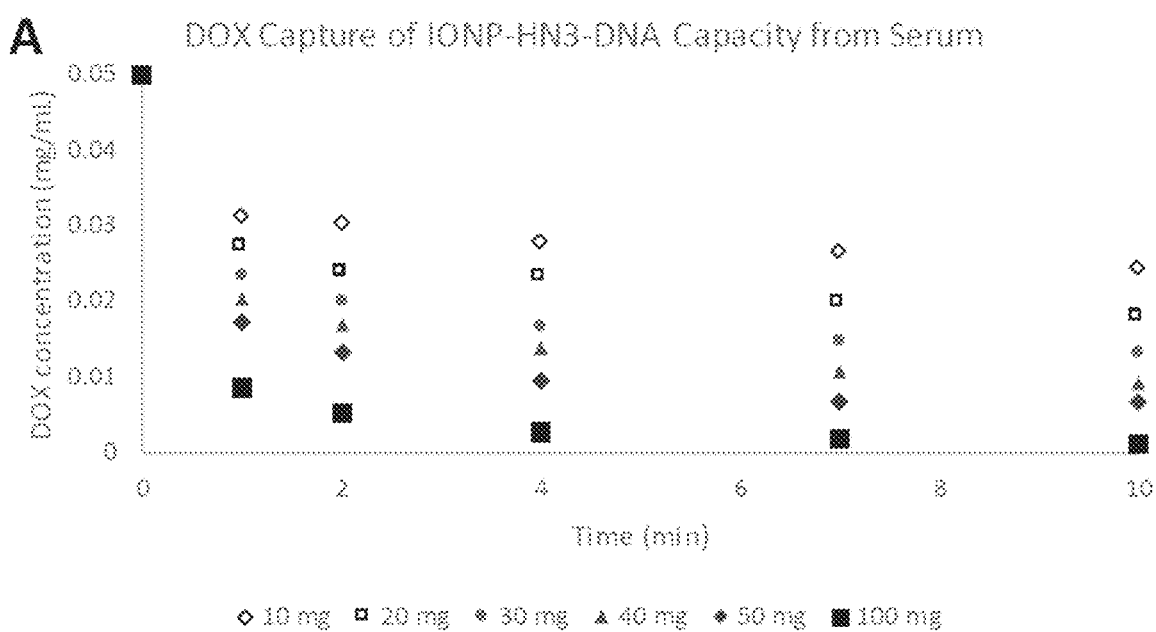
FIG. 4A (Example 1.3) shows doxorubicin capture as a function of the amount of IONP-HN3-DNA from a doxorubicin serum solution (0.5 mg total doxorubicin, 0.05 mg/mL); average of three experiments.
Figure 4A:
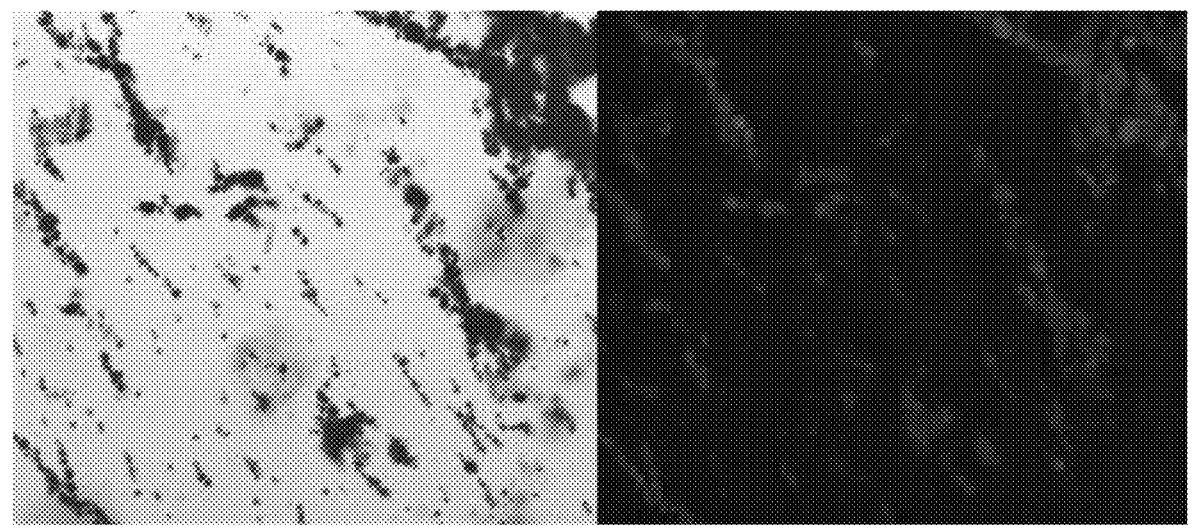

To better understand the DOX-capture capacity of IONP-HN3-DNA, a series of experiments were performed in which particle loading was systematically varied (FIGS. 4A-C). These experiments revealed a roughly linear trend in DOX capture as a function of the amount of particle added, up to a plateau around 100 mg material added per mg DOX, resulting in ~90% DOX capture in 10 minutes. Further DOX capture appeared less favorable after this point. This plateau may be the result of competition with serum binding, which makes that portion of DOX unavailable for capture by these DNA scaffolds, as well as the typical kinetic effects of diminishing concentration. This set of data enables a predictable amount of DOX to be sequestered from solution within a given timeframe based on the amount of particle used. The absorption of DOX onto the scaffolds was further verified by performing confocal fluorescence microscopy (FIG. 4B and FIG. 4C). This technique allowed for visualization of the fluorescence of DOX bound to the surface of the particles using laser excitation.

Figure 5A:
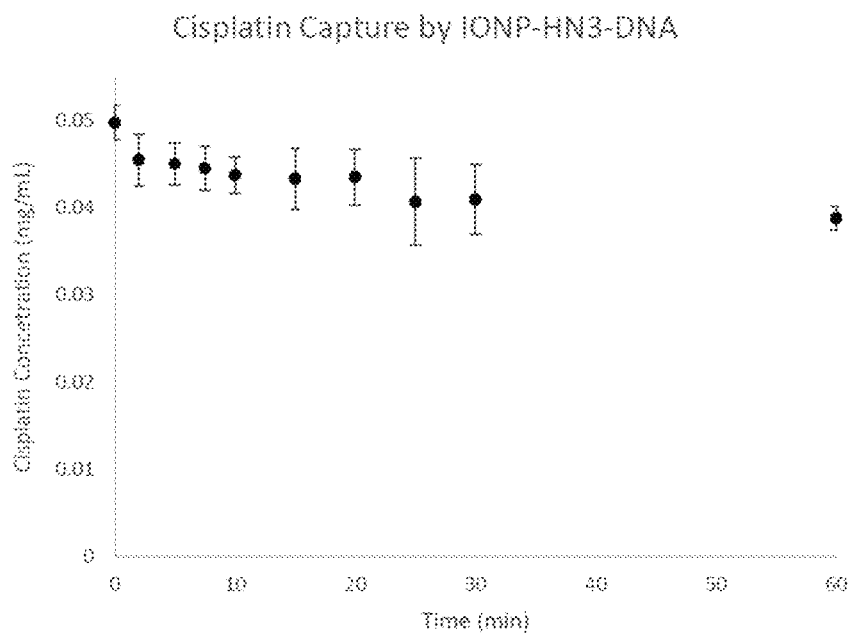
FIG. 5A shows reduction of cisplatin concentration over time due to capture by IONP-HN3-DNA particles, as characterized by ICP-MS. Cisplatin solution (20 mL, 0.05 mg/mL) with 100 mg IONP-HN3-DNA. Average of three runs (error bars=1 standard deviation).
Figure 5B:
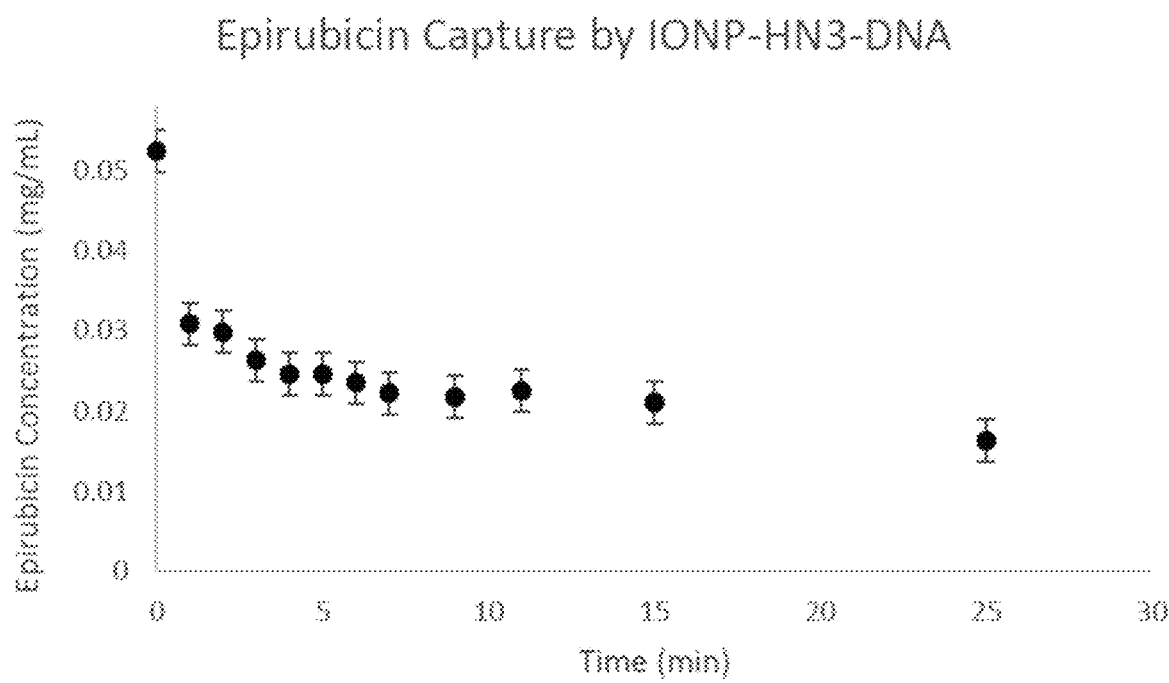
FIG. 5B shows reduction of EPI concentration over time due to capture by IONP-HN3-DNA as characterized by fluorescence measurements. EPI solution (20 mL, 0.05 mg/mL) with 100 mg IONP-HN3-DNA. Average of three runs (error bars=1 standard deviation).
Figure 6A:
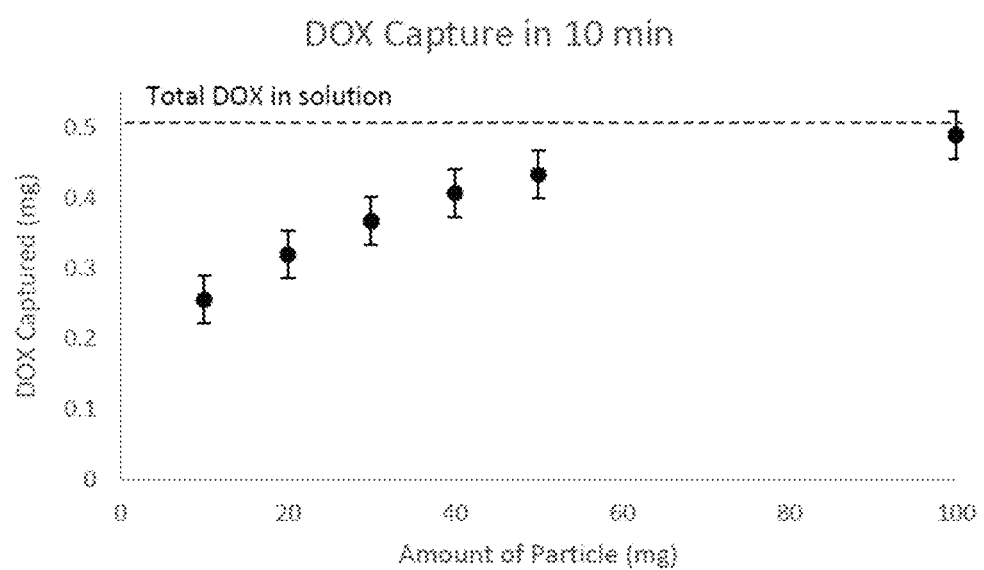
FIGS. 6A-E shows DOX capture as a function of time from human serum (10 mL, 0.05 462 mg/mL, 37° C.) as a function of amount of IONP-HN3-DNA added. Average of 3 runs, 463 error bars=1 standard deviation.
Figure 6B:
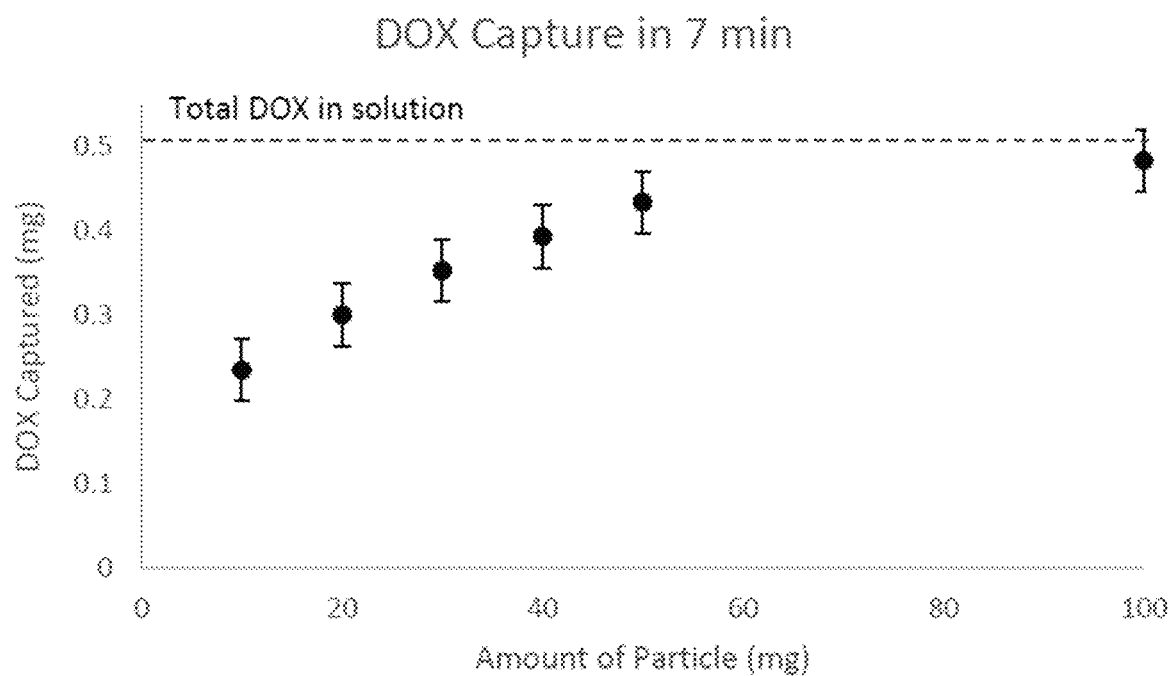
Figure 6C:
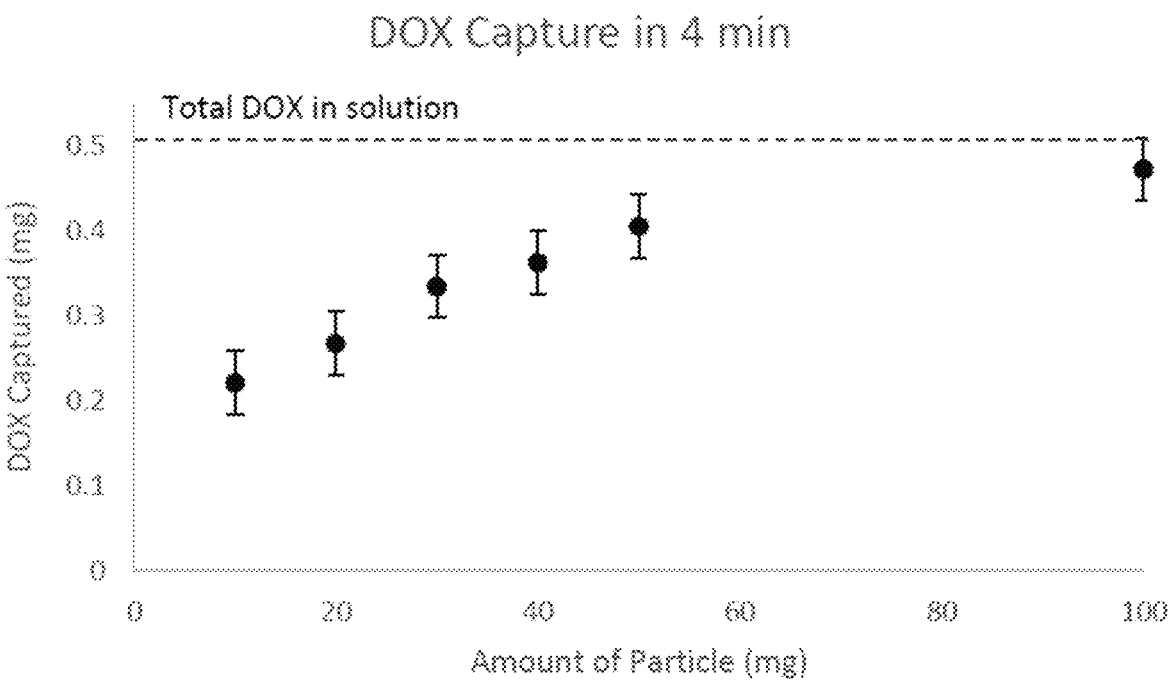
Figure 6D:
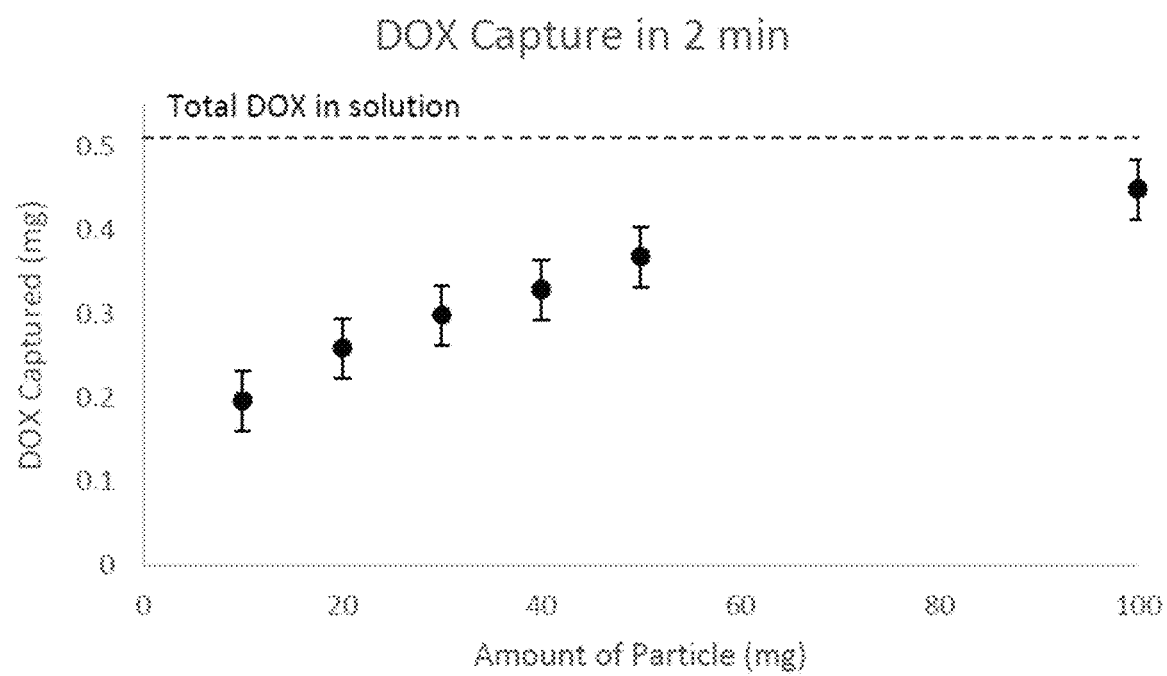
Figure 6E:
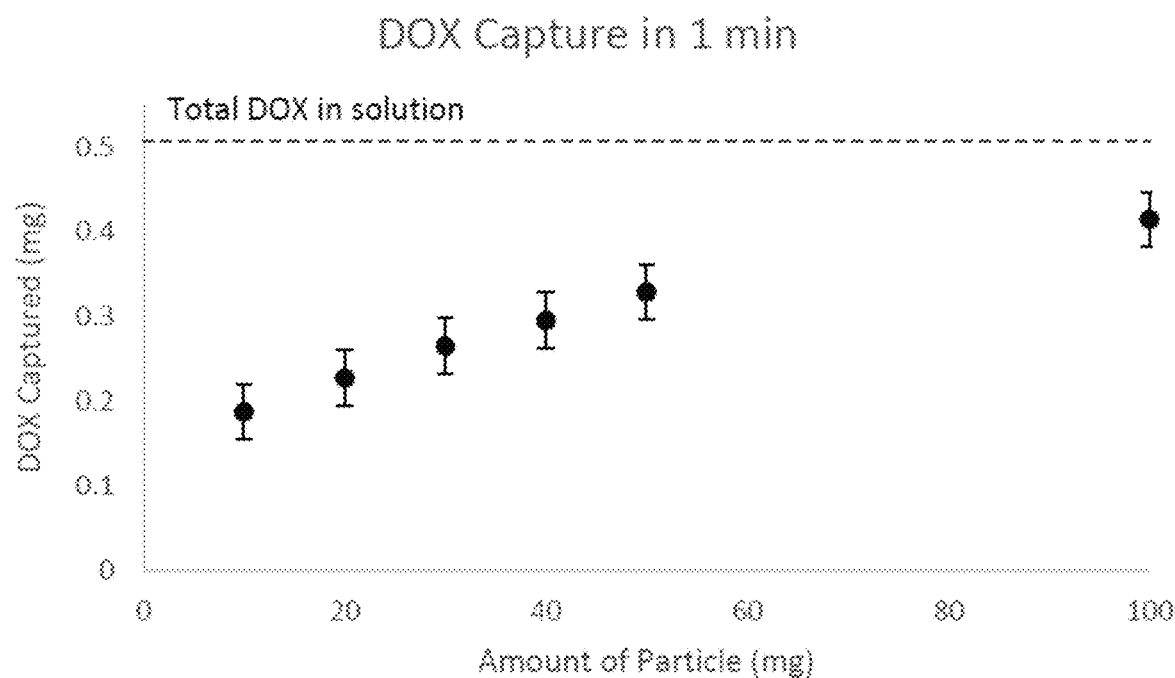

This approach is believed to be general for all DNA-targeting chemotherapy agents. To demonstrate this fact, further experiments were performed on two additional common DNA-targeting chemotherapeutics, cisplatin and EPI. An initial cisplatin-binding experiment was performed in PBS solution with IONP-HN3-DNA and monitored the decrease of cis-platin concentration by inductively coupled plasma-mass spectrometry (ICP-MS). This experiment demonstrated that these—scaffolds were capable of removing cis-platin from solution, but to a lesser degree than DOX. Approximately 20% of the cisplatin was captured from solution over 30 minutes, with little improvement over longer time periods. The presence of captured cisplatin on the surface of the particles was confirmed by x-ray photoelectron spectroscopy. Along with DOX and cisplatin, EPI is among the most commonly used chemotherapeutic agents in the treatment of HCC. The efficacy of these scaffolds for capturing EPI was evaluated using a set of experiments analogous to those used with DOX. While these scaffolds were highly effective at sequestering EPI from serum, only 68% was captured after 25 minutes (as opposed to over 90% with DOX under the same conditions). However, it is important to note that this sequestered amount was still significant, and would lead to a large reduction in unwanted side-effects if achieved in vivo. See also FIGS. 5(A-B) and 6(A-E).

Example 1.4. Device Testing

Figure 7C:
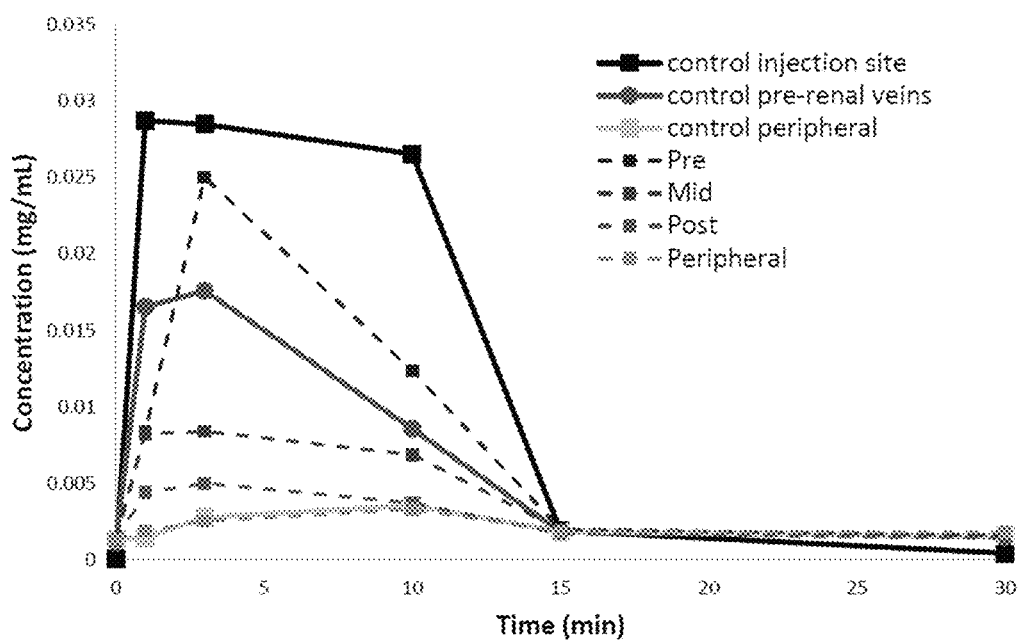
FIG. 7A shows a device (Example 1.4) containing 25 magnets (1 cm×0.5 cm) with IONP-HN3-DNA coating (upper device), and the same device after the in vivo experiment (lower), demonstrating minimal loss of particles after removal of the device.
FIG. 7B shows fluoroscopy images during in vivo porcine experiment demonstrating the inferior vena cava with opacified right renal veins. The device was placed within the inferior vena cava. The sampling catheters were placed immediately proximal to the device, prior to the renal vein, and distal to the device. FIG.
Figure 7A:
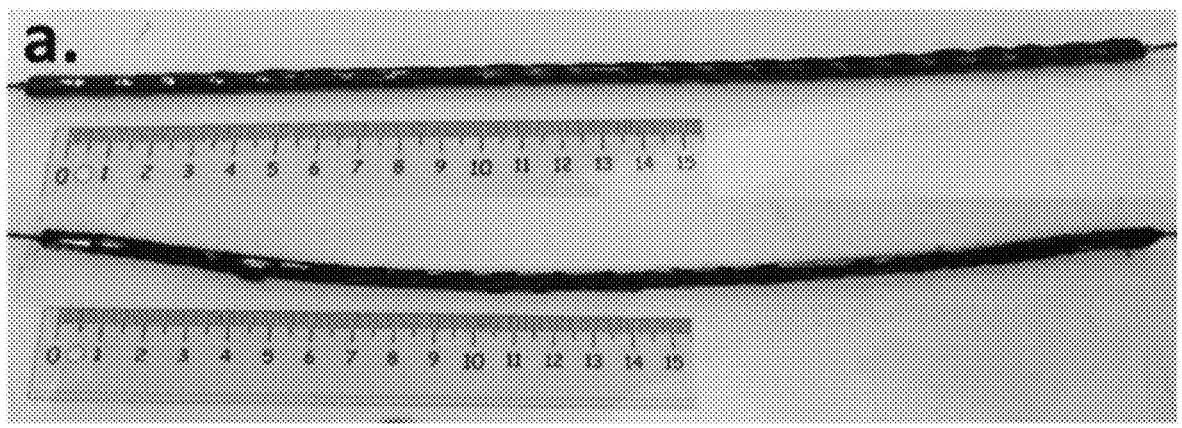
Figure 7B:
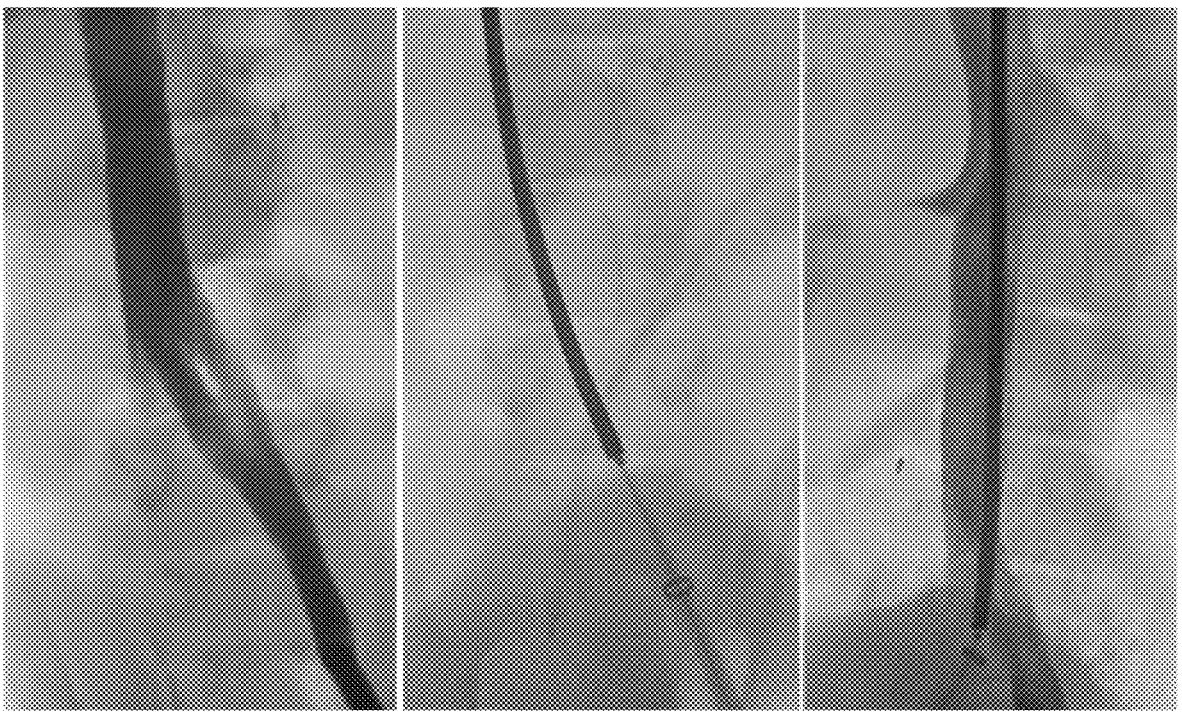

A device (FIG. 7A) consisting of IONP-HN3-DNA magnetically adhered to the surface of cylindrical rare-earth magnets strung along a PTFE coated nitinol wire was evaluated using a closed loop flow model and subsequently tested in vivo using a porcine model. The device was inserted into the inferior vena cava (IVC) and DOX was injected over ten minutes into the left common iliac vein proximal to the device (FIG. 7B). As the drug flowed through the inferior vena cava, it made contact with the bound IONP-HN3-DNA and was captured (FIG. 7C).

Example 1.5 Experimental Materials and Methods for Magnetite Particles

Example 1.5.1 Instrumentation

Fluorescence measurements were made using a 96-well plate on a Molecular devices FlexStation 3 Multi-mode microplate reader. Scanning electron micrographs (SEM) as well as electron dispersive scattering (EDS) measurements were made on a Zeiss 1550VP Field Emission SEM equipped with an Oxford EDS module. Inductively coupled plasma-mass spectrometry (ICP-MS) was carried out on an HP 4500 ICP-MS equipped with a Cetac ASX-500 autosampler, Infrared measurements were made on a Nicolet iS50 Fourier Transform Infrared spectrometer equipped with a DuraScope ATR unit. C, H, N analyses were carried out using a PerkinElmer 2400 Series II MN Elemental Analyzer.

Example 1.5.2 General Procedures

Unless otherwise stated reactions were carried out on the bench. Magnetite ($Fe_3O_4$, 40 nm APS, 99%) was purchased from Nanostructured & Amorphous Materials, Inc. Silane reagents were purchased from Gelest, Inc. Genomic DNA (isolated from Herring sperm), human serum (OptiClear), and cisplatin were purchased from Sigma Aldrich. Doxorubicin was purchased from LC Labs and epirubicin was purchased from Biotang Inc. Potassium tetrachloroplatinate was purchased from Pressure Chemicals. All reagents, not otherwise mentioned were purchased from Sigma Aldrich, and were used without further purification.

Example 1.5.3 Device Construction 25 cylindrical rare earth magnets (N52 grade, 5 mm OD×1 mm ID×5 mm L, magnetized through the diameter) were strung along the length of a PTFE coated nitinol wire (Terumo Glidewire). IONP-HN3-DNA (1.0 g) was suspended in water and subsequently magnetically adhered to the surface of this device.

Example 1.5.4 Flow Model Experiments

A closed-circuit flow model was used to measure doxorubicin clearance in a setting the simulates suprahepatic inferior vena cava conditions. In this model, the porcine blood is circulated through the polyvinyl chloride tubing at a rate of approximately 150 mL/min. The tubing size matches the average human hepatic vein measuring 1.2 cm as described previously. Testing was performed with 200 ml porcine blood and samples were obtained from the tubing downstream from the device.

Example 1.5.5 In Vivo Porcine Experiments

In vivo device testing was performed in farm swine (n=1, 45-50 kg), which was under humane care. Experimentation was under compliance with UCSF IACUC protocols. The animal was monitored with blood pressure, pulse oximetry, heart rate, and electrocardiogram while under general anesthesia with isoflurane. Using fluoroscopic guidance, an 18Fr sheath was placed into the left external iliac vein for introduction of the device. A pre-device sampling catheter was introduced through the right external iliac vein with the tip terminating in the left common iliac vein near the bifurcation. An additional catheter was introduced via the right internal jugular vein with the tip distal to the device in the IVC (post-device). The mid-device catheter and peripheral catheters were introduced through the left internal jugular vein. Prior to the start of the experiments, patency of the venous system was demonstrated using contrast injection (Omnipaque). Doxorubicin was injected over ten minutes at a rate of 2.5 ml/min into the left common iliac vein proximal to the magnetic device. The pre-device doxorubicin concentration was measured by sampling with a 5 Fr catheter downstream of the doxorubicin infusion. Blood aliquots were taken proximal to, adjacent to the midpoint of, and distal to the device using separate catheters. To clear the sampling catheters, 2 mL of blood was drawn immediately prior to taking the aliquot (3 mL). The blood samples were placed on ice until they were centrifuged to isolate the plasma fraction for analysis. A control experiment was also performed using the same procedures but with no device inserted.

Example 1.5.6 Particle Synthesis

IONP-Pt:

3.31 g Magnetite ($Fe_3O_4$) was dried in vacuo at 120° Celsius. Upon cooling, the sealed material was introduced into an inert atmosphere nitrogen glovebox. To the magnetite was added 23 mL anhydrous toluene along with 4 mL N-(2-aminoethyl)-3-aminopropyltrimethoxysilane. The reaction was mechanically stirred on the bench at 110° Celsius for 2 hours and subsequently dried in vacuo at 110° Celsius for 20 hours. The reaction mixture along with 1.0 g $K_2PtCl_4$, was stirred at 70° Celsius for 21 minutes and then washed three times with water. Following this, the mixture was diluted to a total volume of 450 mL with 18.2 MΩ water was treated with 1.3 g KCl and an additional 10 mL water.

IONP-Pt-DNA:

IONP-Pt materials along with 5.1 g deoxyribonucleic acid from herring sperm were mechanically stirred in 450 mL 18.2 MΩ water at 37° Celsius for 20 hours. To ensure covalent attachment as opposed to being physically adsorbed, the particles were isolated from the reaction mixture, washed three times under vigorous mechanical stirring with 18.2 MΩ water (400 mL), frozen, and lyophilized to afford 3.08 g IONP-Pt-DNA.

IONP-NH2:

4.2 g of magnetite ($Fe_3O_4$) was dried in vacuo at 120° Celsius. The $Fe_3O_4$ was allowed to cool to room temperature under vacuum. To the $Fe_3O_4$ was added 25 mL toluene (freshly dried over magnesium sulfate) and 3.2 mL 4-aminobutyltriethoxysilane. The reaction was sealed and stirred mechanically for 2 hours at 120° Celsius. The reaction was removed from heat and the particles were isolated from the toluene solution. The reaction mixture was washed once with toluene and subsequently dried in vacuo at 120° Celsius for 1 hour and 45 minutes. 4.02 g of IONP-HN3 was isolated.

IONP-HN3-DNA:

3.4750 g IONP-HN3 was added to a vial along with 1.02 g tris(2-chloroethyl)amine hydrochloride and dimethylformamide (30 mL). The reaction was stirred mechanically for 1 hour at room temperature at which point, the particles were isolated from the dimethylformamide. The particles were then washed three times with dimethylformamide. The isolated particle as well as 3.35 g deoxyribonucleic acid from herring sperm were transferred into a flask along with 400 mL 18.2 MΩ water. The reaction was mechanically stirred at 38° Celsius for 17 hours and 45 minutes. To ensure covalent attachment, the particles were then washed thoroughly under vigorous mechanical stirring three times with 18.2 MΩ water (400 mL) and 1 magnetic separation. The particles were then frozen in liquid nitrogen and lyophilized to afford 3.79 g of IONP-HN3-DNA.

Example 1.5.7 Representative Binding Studies

DOX:

To a scintillation vial was added 19 mL human serum. Drug was injected at a concentration of 1 mg/mL from a concentrated stock, to bring the total concentration to approximately 0.05 mg/mL. An initial time point was taken before drug capture. DNA particles (100±5 mg) were added to the serum mixture, which was constantly, mechanically stirred. 20 seconds before a time point was taken, a strong, rare earth, magnet was used to isolate the particles, at which point, a 100 μL aliquot is taken and placed in a 96 plate microplate well. The solutions were then measured by way of fluorescence on a microplate reader.

Cisplatin:

Phosphate buffered saline solution (19 mL) was added to a scintillation vial. Cisplatin solution (1 mL, 1 mg/mL solution) was then injected, followed by 117±5 mg of IONP-HN3-DNA, and the mixture was mechanically stirred over the course of an hour. At predetermined time points the magnetic materials were temporarily isolated using an external magnet so that 100 μL aliquots could be taken, which were diluted 200× in 2% nitric acid solution and subsequently analyzed by ICP-MS to determine the concentration of platinum remaining in solution.

EPI:

Human serum (19 mL) was added to a scintillation vial. EPI solution in water (1 mL, 1 mg/mL solution) was then added. The particles (100±5 mg IONP-HN3-DNA) were then added and the solution was mechanically stirred over the course of 25 minutes. At predetermined time points, the magnetic materials were temporarily isolated using an external magnet and 100 μL aliquots were taken, which were subsequently diluted 100× in water and analyzed by fluorescence on a microplate reader in order to characterize the amount of EPI remaining in solution Example 2. Polymer Scaffolding The present disclosure describes three general synthetic approaches for preparing genomic DNA functionalized architected materials fabricated via additive manufacturing. Each approach involved the attachment of amines or thiols onto the surface of 3D polymeric structures, as shown in FIGS. 9(A-C), 10, and 11. In general, a thiolated compound containing either the Boc-protected amine or Boc-protected diamine is reacted with the multifunctional acrylate monomer.

Example 2.1.1: HN3 Method

Amines were first introduced onto the surface of polymer structures fabricated via additive manufacturing. These structures were made in a variety of ways, including but not limited to the following:

a) A multifunctional acrylate was first reacted with a thiol containing a Boc-protected amine using the thiol-Michael addition reaction. The functionalized acrylate was then photopolymerized into a 3D structure. The Boc-protected amines on the surface of the material were then deprotected to give a surface populated with primary amines.

b) Acrylate based polymer structures fabricated via additive manufacturing were then reacted with ethylene diamine under reflux to introduce primary amines onto the surface. The aminated surface of the material was treated with tris(2-chloroethyl)amine hydrochloride, the hydrochloride salt of the nitrogen mustard HN3, to create a scaffold for DNA functionalization. Upon deprotonation, the HN3 molecules underwent aziridinium formation, which reacted with the nucleophilic moieties of the genomic DNA. The bound DNA was able to bind to drugs.

All compounds used in the present invention were purchased commercially (Sigma-Aldrich Chemical Co.). General thiol-Michael addition reaction: Each reaction was conducted in a closed 20 ml vial equipped with a magnetic stir bar. The acrylate monomer was added along with the thiolated compound and a catalytic amount of base/nucleophile. The solution was then heated at 45° C. and left to stir overnight.

Preparation of photoresin: The modified acrylate monomers were then mixed with an appropriate photoinitiator and solvent.

Example 2.1.2. Doxorubicin Capture Via 3D Scaffolds

Example 2.1.2.1. Preparation of Scaffolds Fabricated Via Two-Photon Lithography 2 mol of 2-(Boc-amino)ethanethiol and 1 mol of dipentaerythritol hexaacrylate were reacted via the thiol-Michael addition reaction described above. The structural form of one of the products is shown below in FIG. 12. The thiol-Michael adducts were then mixed with 7-diethyl-amino-2-thenoyl coumarin in dichloromethane to form a photosensitive resin. Two-photon lithography was then as the laser-induced photopolymerization method to fabricate the architected structure. A representative scanning electron microscope (SEM) image of an architected structure fabricated with the photoresist is shown in FIG. 13.

The surface of the architectured structure was then deprotected in a 50/50 vol % stirred solution of trifluoroacetic acid and dichloromethane for 90 minutes, then washed in a solution of sodium bicarbonate to neutralize any acid on the surface, followed by immersion in water to remove any salts formed. The resulting material was immersed in a stirred solution of HN3.HCl in DMF at a concentration of 15 mg/ml for 1 hours. After the reaction was complete, the material was washed with DMF and then DCM to rinse off any excess HN3. X-ray photoelectron spectroscopy (XPS) of the material confirmed the presence of chlorine, indicating the success attachment of HN3 onto the material. The material was then immersed in a stirred solution of genomic DNA (Salmon DNA, as purchased from Sigma Aldrich) in phosphate buffered solution at a concentration of 5 mg/ml for 24 hours. The material was then washed in deionized water to remove any physically adsorbed DNA.

Example 2.1.2.2. Testing of Materials

To test the effectiveness of the genomic DNA in binding to doxorubicin, the genomic DNA functionalized material was immersed in a solution of doxorubicin (0.025 mg/ml in PBS) and aliquots of the solution taken every minute for a total time of ten minutes. A final aliquot was taken at the fifteen minutes mark. By measuring the intensity of the fluorescence over time and matching it to a calibration curve, the change in concentration can be measured. FIG. 15 shows the change in concentration over time and as seen, approximately 10% of the doxorubicin in solution was removed. Since doxorubicin naturally fluoresces, fluorescence microscopy was conducted on the material to verify that the doxorubicin was bound to the material. FIGS. 16A-B show the fluorescence microscopy images of the material, confirming that doxorubicin sequestered from solution was bound to the scaffold. To adjust for the autofluorescence from the photoinitiator, a control was used to determine the intensity from the photoinitiator. That intensity value was then subtracted from that of the doxorubicin-bound material to determine the actual intensity values from the doxorubicin. Both sets of fluorescence images were plotted with the same intensity scales to reflect the relative difference in intensity between the control and the doxorubicin bound material.

Example 2.1.2.3. Preparation of Scaffolds Fabricated Via Projections Micro-Stereolithography 1 mol of 2-(Boc-amino)ethanethiol and 1 mol of pentaerythritol tetraacrylate were reacted via the thiol-Michael addition reaction described above. The thiol-Michael adducts (75 wt %) are then mixed with neopentyl glycol (~23 wt %), ethyl (2,4,6-trimethylbenzoyl) phenyl phosphinate (~0.5 wt %) and 2,2'-(2,5-thiophenediyl)bis(5-tertbutylbenzoxazole) (~0.2 wt %) in dichloromethane (~1 wt %) to form a photosensitive resin. The photoresin was then used in an Autodesk Ember printer to fabricate 3D structures. In this example, simple plates, 5 mm (W)×5 mm (L)×0.5 mm (H) were made.

The surface of the architectured structure was then deprotected in a 50/50 vol % solution of trifluoroacetic acid and dichloromethane for 10 minutes. After deprotection, the samples were soaked in a 1M solution of sodium hydroxide for 60 minutes and the material was then immersed in a stirred solution of HN3.HCl in DMF at a concentration of 15 mg/ml for 3 hours. The samples were then rinsed in DMF and dried with a nitrogen gun. The HN3 functionalized material was then immersed in a stirred solution of genomic DNA (Salmon DNA, as purchased from Sigma Aldrich) (5 mg/mL) and sodium bicarbonate (60 mg/mL) in phosphate buffered solution for 24 hours. The material was then washed in deionized water to remove any physically adsorbed DNA.

Example 2.1.2.4. Testing of Materials

To test the effectiveness of the genomic DNA in binding to doxorubicin, the genomic DNA functionalized material was immersed in a solution of doxorubicin (0.025 mg/ml in PBS) and aliquots of the solution taken at the one, two, five and ten minute. By measuring the intensity of the fluorescence over time and matching it to a calibration curve, the change in concentration was measured. FIG. 17 shows the change in concentration over time and as shown, approximately 10% of the doxorubicin in solution was removed. To verify that it was the genomic DNA that was binding to the doxorubicin, a control sample that was not functionalized with genomic DNA was immersed into a solution of doxorubicin as well. The control sample treated in this way did not have any noticeable color change, indicating no binding.

Example 2.2. Cisplatin Method

In procedures analogous to those described in Example 1.5.6, diamines, dithiols and thioethers were first introduced onto the surface of the polymer structure fabricated via additive manufacturing. These were achieved in a variety of ways, including but not limited to the following: a) A multifunctional acrylate was first reacted with a thiol containing Boc-protected diamines using the thiol-Michael addition reaction to install a chelating diamine functionality. The functionalized acrylate was then photopolymerized into a 3D structure. The Boc-protected diamines on the surface of the material were then deprotected to give a surface primed for chelation via the diamines. b) A multifunctional acrylate was first reacted with a thiol containing a Boc-protected amine using the thiol-Michael addition reaction. The functionalized acrylate was then made into a 3D structure via photopolymerization. The Boc-protected amines on the surface of the material were then deprotected to give a surface populated with primary amines. Thiirane was used to react with these primary amines to grow polythioether chains off the surface. The material was treated with potassium tetrachloroplatinate to create a cisplatin analogue that reacted with the genomic DNA.

Example 2.2. Other Polymer Linkages

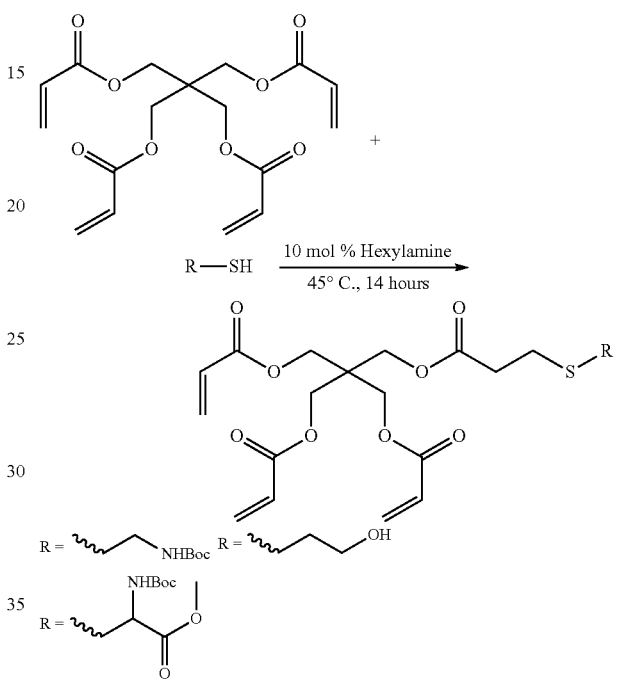

The general Michael addition of thiols to acrylate linkages were used to prepare a host of pendant reactive groups, three of which are shown above. The functionalized acrylate was synthesized by reacting pentaerythritol tetraacrylate with the corresponding thiol in a 1:1 mol ratio via the thiol-Michael reaction. Pentaerythritol tetraacrylate (1.0 equiv., 3 g, 8.51 mmol), thiol (1.0 equiv., 8.51 mmol), and hexylamine (0.1 equiv. 0.112 mL, 0.85 mL) were added to a 20 mL scintillation vial, The reaction mixture became warm and homogeneous within two minutes and was stirred at 40° C. for 14 hours. Completion of the reaction was verified by 41 and $^{13}$C NMR and the products were used without further purification. A photosensitive composition was prepared by mixing the corresponding functionalized acrylate (typically 0.30 g, 90.4 wt %) with 7-diethylamino-3-thenoylcoumarin (5.6 mg, 1.6 wt %), an efficient two-photon photoinitiator in dichloromethane, in dichloromethane (20 μL, 8.0 wt %). The functional compositions were stored under yellow light, displaying no observable change in photoreactivity over a period of three months. A range of nano-architected structures with different cell geometries were prepared, including lattice cells of ranging from about 20 μm to 70 using rastered laser scans in the x-y plane and the slicing distances in the z-direction set at 200 nm, the laser power being set as 20 mW, and a writing speed at 2 cm/sec. See, e.g., FIG. 14. The compositions were confirmed by $^1$H and $^{13}$C-NMR, EDX, and XPS (not shown). These structures, with pendant hydroxyls can be reacted further with aminosiloxanes and/or the Boc-protected amines can be deprotected to form amines, which can further be functionized as shown in Example 1.

The following references may be helpful in understanding some of the concepts described herein:

1. C. S. Cleeland et al., Reducing the toxicity of cancer therapy: recognizing needs, taking action. *Nat. Rev. Clin. Oncol.* 9, 1-8 (2012).
2. N. P. Tatonetti, P. P. Ye, R. Daneshjou, R. B. Altman, *Sci Transl Med*, in press, doi:10.1126/scitranslmed.3003377.
3. D. Bovelli, G. Plataniotis, F. Roila, Cardiotoxicity of chemotherapeutic agents and radiotherapy-related heart disease: ESMO clinical practice guidelines. *Ann. Oncol.* 21, 277-282 (2010).
4. S. F. Altekruse, K. A. McGlynn, M. E. Reichman, Hepatocellular carcinoma incidence, mortality, and survival trends in the United States from 1975 to 2005. *J. Clin. Oncol.* 27, 1485-1491 (2009).
5. International Agency for Research on Cancer, World Cancer report 2008. *Cancer Control.* 199, 512 (2008).
6. J. Belghiti, R. Kianmanesh, Surgical treatment of hepatocellular carcinoma. *HPB (Oxford).* 7, 42-49 (2005).
7. L. Marelli et al., Transarterial therapy for hepatocellular carcinoma: Which technique is more effective? A systematic review of cohort and randomized studies. *Cardiovasc. Intervent. Radiol.* 30, 6-25 (2007).
8. K. Cheung-Ong, G. Giaever, C. Nislow, DNA-Damaging Agents in Cancer Chemotherapy: Serendipity and Chemical Biology. *Chem. Biol.* 20, 648-659 (2013).
9. G. Minotti, P. Menna, E. Salvatorelli, G. Cairo, L. Gianni, Anthracyclines: molecular advances and pharmacologic developments in antitumor activity and cardiotoxicity. *Pharmacol. Rev.* 56, 185-229 (2004).
10. M. Ryberg et al., Epirubicin cardiotoxicity: An analysis of 469 patients with metastatic breast cancer. *J. Clin. Oncol.* 16, 3502-3508 (1998).
11. R. P. Miller, R. K. Tadagavadi, G. Ramesh, W. B. Reeves, Mechanisms of cisplatin nephrotoxicity. *Toxins (Basel).* 2, 2490-2518 (2010).
12. D. Wang, S. J. Lippard, Cellular processing of platinum anticancer drugs. *Nat. Rev. Drug Deliv.* 4, 307-320 (2005).
13. A. M. Rahman, S. W. Yusuf, M. S. Ewer, Anthracycline-induced cardiotoxicity and the cardiac-sparing effect of liposomal formulation. *Int. J. Nanomedicine.* 2, 567-583 (2007).
14. A. U. Buzdar, C. Marcus, T. L. Smith, G. R. Blumenschein, Early and delayed clinical cardiotoxicity of doxorubicin. *Cancer.* 55, 2761-2765 (1985).
15. E. T. H. Yeh, C. L. Bickford, Cardiovascular Complications of Cancer Therapy. *J. Am. Coll. Cardiol.* 53, 2231-2247 (2009).
16. A. S. Patel et al., Development and Validation of Endovascular Chemotherapy Filter Device for Removing High-Dose Doxorubicin: Preclinical Study. *J. Med. Device.* 8, 0410081-0410088 (2014).
17. E. A. Tsochatzis, G. Germani, A. K. Burroughs, Transarterial Chemoembolization, Transarterial Chemotherapy, and Intra-arterial Chemotherapy for Hepatocellular Carcinoma Treatment. *Semin. Oncol.* 37, 89-93 (2010).
18. X. C. Chen et al., Block Copolymer Membranes for Efficient Capture of a Chemotherapy Drug. *ACS Macro Lett.,* 936-941 (2016).
19. A. Kumar, O. Larsson, D. Parodi, Z. Liang, Silanized nucleic acids: a general platform for DNA immobilization. *Nucleic Acids Res.* 28, E71 (2000).
20. S. J. Hurst et al., Synthetically programmable DNA binding domains in aggregates of DNA-functionalized gold nanoparticles. *Small.* 5, 2156-2161 (2009).
21. G. Cohen, J. Deutsch, J. Fineberg, A. Levine, Covalent attachment of hybridizable oligonucleotides to glass supports. *Nucleic Acids Res.* 25, 911-912 (1997).
22. M. Beier, J. D. Hoheisel, Versatile derivatisation of solid support media for covalent bonding on DNA-microchips. *Nucleic Acids Res.* 27, 1970-1977 (1999).
23. K. Shinozuka, Y. Seto, H. Kawata, H. Sawai, Bifunctional labelling of DNA with Tris(2-aminoethyl) amine-dervied novel fluorescent agent. *Bioorg. Med. Chem. Lett.* 3, 2883-2886 (1993).
24. G. Yao et al., Clicking DNA to gold nanoparticles: poly-adenine-mediated formation of monovalent DNA-gold nanoparticle conjugates with nearly quantitative yield. *NPG Asia Mater.* 7, e159 (2015).
25. C. A. Mirkin, R. L. Letsinger, R. C. Mucic, J. J. Storhoff, A DNA-based method for rationally assembling nanoparticles into macroscopic materials. *Nature.* 382 (1996), pp. 607-609.
26. R. J. Macfarlane et al., Nanoparticle superlattice engineering with DNA. *Science.* 334, 204-8 (2011).
27. Y. Song et al., Multimodal Gadolinium-Enriched DNA Gold Nanoparticle Conjugates for Cellular Imaging. *Angew. Chem. Int. Ed. Engl.* 48, 9143-9147 (2009).
28. R. J. Lipshutz, S. P. Fodor, T. R. Gingeras, D. J. Lockhart, High density synthetic oligonucleotide arrays. *Nat. Genet.* 21, 20-4 (1999).
29. H. Jo, C. Ban, Aptamer-nanoparticle complexes as powerful diagnostic and therapeutic tools. *Exp. Mol. Med.* 48, e230 (2016).
30. E. D. Smolensky, K. L. Peterson, E. a Weitz, C. Lewandowski, C. Pierre, Magnetoluminescent Light Switches—Dual Modality in DNA Detection Eric. *J. Am. Chem. Soc.* 135, 8966-8972 (2013).
31. Z. H. Siddik, Cisplatin: mode of cytotoxic action and molecular basis of resistance. *Oncogene.* 22, 7265-79 (2003).
32. A. Polavarapu, J. A. Stillabower, S. G. W. Stubblefield, W. M. Taylor, M. H. Baik, The mechanism of guanine alkylation by nitrogen mustards: A computational study. *J. Org. Chem.* 77, 5914-5921 (2012).
33. D. Agudelo et al., Probing the binding sites of antibiotic drugs doxorubicin and N-(trifluoroacetyl) doxorubicin with human and bovine serum albumins. *PLoS One.* 7, 1-13 (2012).
34. D. Agudelo, P. Bourassa, G. B??rub??, H. A. Tajmir-Riahi, Intercalation of antitumor drug doxorubicin and its analogue by DNA duplex: Structural features and biological implications. *Int. J. Biol. Macromol.* 66, 144-150 (2014).

As those skilled in the art will appreciate, numerous modifications and variations of the present disclosure are possible in light of these teachings, and all such are contemplated hereby. For example, in addition to the embodiments described herein, the present disclosure contemplates and claims those inventions resulting from the combination of features of the disclosure cited herein and those of the cited prior art references which complement the features of the present disclosure. Similarly, it will be appreciated that any described material, feature, or article may be used in combination with any other material, feature, or article, and such combinations are considered within the scope of this disclosure.

The disclosures of each patent, patent application, and publication cited or described in this document are hereby incorporated herein by reference, each in its entirety, for all purposes, or at least for the context in which the reference was cited.

What is claimed:

1. A structured composition comprising DNA operatively linked to a scaffold through an organic polymer surface and/or a hydroxylated inorganic surface of the scaffold, wherein the DNA is operatively linked to the organic polymer surface or hydroxylated inorganic surface by attachment to a linking group, wherein:
   (a) the organic polymer surface comprises a lithographically patterned organic polymer; or
   (b) the scaffold comprises a three-dimensionally (3D) photopolymerized patterned polymer structure; or
   (c) the linking group is covalently bound to the organic polymer surface, the covalent bond resulting from the co-polymerization of an unsaturated moiety of a linker group precursor with a prepolymer of the organic polymer to form the linking group pendant to the surface; or
   (d) the organic polymer surface comprises a polyhydroxylated organic polymer comprising (co)polymerized polyvinyl alcohol, polyalkylhydroxy(meth)acrylate, polyhydroxyalkyl(meth)acrylamide, monoglycerol(meth)acrylate, monoglycerol(meth)acrylamide, or a combination thereof, or (co)polymerized (meth)acrylate linkages; or
   (e) the linking group is covalently bound to the hydroxylated inorganic surface.

2. The structured composition of claim 1, where the scaffold is in the form of a sheet, tube, microparticle, macroparticle, nanoparticle, nanotube, nanofiber, microfiber, fiber, wire, membrane, mesh, or web.

3. The structured composition of claim 2, wherein the structured composition is contained in or on a medical device.

4. The structured composition of claim 3, wherein the structured composition is in a form of a structured fiber, wire, mesh, or membrane.

5. The structured composition of claim 4, wherein the structured composition is incorporated into a catheter, stent, cannula, or like flexible tubular device capable of being delivered locally to a position within the vascular system of a stent.

6. The structured composition of claim 5, wherein the structured composition is alternatively extendible from and retractable into the catheter, stent, cannula, or like flexible tubular device.

7. The structured composition of claim 5, wherein the exterior surface of the catheter, stent, cannula, or like flexible tubular device is coated with the structured composition.

8. The structured composition of claim 1, wherein the linking group comprises one or more internal covalent aliphatic or aromatic amide, amine, ester, ether, thioamide, thioester, or thioether bonds, or a coordinative ligand linkage to a transition metal.

9. The structured composition of claim 1, wherein the DNA is genomic DNA.

10. The structured composition of claim 1, wherein the DNA is linked to the linking group by:
    (a) a covalent aliphatic or aromatic amide, amine, ester, ether, thioamide, thioester, or thioether bond; or
    (b) intercalation or an electrostatic, pi-pi, and/or hydrogen-bonding mechanisms with a moiety on the linking group; or
    (c) bonding to a cis-platin-like moiety covalently attached to the linking group.

11. The structured composition of claim 1, wherein the scaffold and/or the organic or hydroxylated inorganic surface comprises the organic polymer surface comprising the polyhydroxylated organic polymer comprising (co)polymerized (meth)acrylate linkages.

12. The structured composition of claim 1, wherein the scaffold and/or the organic polymer surface or hydroxylated inorganic surface comprises the lithographically patterned organic polymer.

13. The structured composition of claim 1, wherein the scaffold comprises the three-dimensionally (3D) photopolymerized patterned polymer structure.

14. The structured composition of claim 1, wherein the scaffold and/or the organic polymer surface or hydroxylated inorganic surface comprises the organic polymer and the linking group is covalently bound to the organic polymer surface, the covalent bond resulting from the co-polymerization of an unsaturated moiety of a linker group precursor with a prepolymer of the organic polymer to form the linking group pendant to the surface.

15. The structured composition of claim 1, wherein the linking group is covalently bound to the organic surface comprising the polyhydroxylated organic polymer.

16. The structured composition of claim 1, wherein the linking group is covalently bound to the organic polymer surface by an aliphatic or aromatic amide, amine, ester, ether, thioamide, thioester, thioether or silyl ether linkage.

17. The structured composition of claim 1, wherein the scaffold and/or the organic polymer surface or hydroxylated inorganic surface comprises the polyhydroxylated organic polymer comprises (co)polymerized polyvinyl alcohol, polyalkylhydroxy(meth)acrylate, polyhydroxyalkyl(meth)acrylamide, monoglycerol(meth)acrylate, monoglycerol(meth)acrylamide, or a combination thereof.

18. The structured composition of claim 1, wherein the scaffold and/or the organic polymer surface or hydroxylated inorganic surface comprises the organic polymer surface comprising the polyhydroxylated organic polymer comprising (co)polymerized 2 hydroxyethyl(meth)acrylate, 2-hydroxypropyl(meth)acrylate, 3-hydroxypropyl(meth)acrylate, 2-hydroxybutyl(meth)acrylate, 3-hydroxybutyl(meth)acrylate, and 4-hydroxybutyl(meth)acrylate, and glycerol mono(meth)acrylate.

19. The structured composition of claim 1, wherein the scaffold and the organic polymer surface or hydroxylated inorganic surface comprises a hydroxylated metal or hydroxylated metalloid.

20. The structured composition of claim 1, wherein the scaffold and the organic polymer surface or hydroxylated inorganic surface comprises a hydroxylated metal oxide or hydroxylated metalloid oxide.

21. The structured composition of claim 20, wherein the linking group is covalently bound to the hydroxylated inorganic surface.

22. The structured composition of claim 21, wherein the hydroxylated inorganic surface comprises a hydrous oxide of Al, B, Ca, Cr, Fe, Mg, Ni, Si, Sn, Ti, Zn, or Zr.

23. The structured composition of claim 21, wherein the hydroxylated inorganic surface comprises a hydroxylated silicate glass or clay.

24. The structured composition of claim 21, wherein the linker group is covalently attached to the hydroxylated inorganic surface by a metal silyl ether linkage.

25. The structured composition of claim 1, further comprising a captured drug, wherein the captured drug is bonded or otherwise attached to the DNA.

26. The structured composition of claim 25, wherein the captured drug comprises doxorubicin (DOX), epirubicin (EPI), daunorubicin, a nitrogen mustard, a nitrosourea, an alkyl sulfonate, a triazine, an ethylenimine, trabectedin, or a Pt-drug.

27. The structured composition of claim 1, wherein the structured composition is in physical contact with a physiological fluid.

28. The structured composition of claim 27, wherein the physiological fluid is saline, blood, serum, or blood plasma.

29. A method of removing drugs from a physiological fluid, the method comprising contacting the physiological fluid with a structured composition for a time sufficient to remove at least a portion of the drug from the physiological fluid, wherein the structured composition comprises DNA operatively linked to a scaffold through an organic polymer surface and/or hydroxylated inorganic surface of the scaffold, wherein the DNA is linked to the organic polymer surface or hydroxylated inorganic surface by attachment to a linking group, wherein:
(a) the organic polymer surface comprises a lithographically patterned organic polymer; or
(b) the scaffold comprises a three-dimensionally (3D) photopolymerized patterned polymer structure; or
(c) the linking group is covalently bound to the organic polymer surface, the covalent bond resulting from the co-polymerization of an unsaturated moiety of a linker group precursor with a prepolymer of the organic polymer to form the linking group pendant to the surface; or
(d) the organic polymer surface comprises a polyhydroxylated organic polymer comprising (co)polymerized polyvinyl alcohol, polyalkylhydroxy(meth)acrylate, polyhydroxyalkyl(meth)acrylamide, monoglycerol (meth)acrylate, monoglycerol(meth)acrylamide, or a combination thereof, or (co)polymerized (meth)acrylate linkages; or
(e) the linking group is covalently bound to the hydroxylated inorganic surface.

30. The method of claim 29, where the scaffold is in the form of a sheet, tube, microparticle, macroparticle, nanoparticle, nanotube, nanofiber, microfiber, fiber, wire, membrane, mesh, or web.

31. The method of claim 30, wherein the structured composition is contained in or on a medical device.

32. The method of claim 31, wherein the structured composition is in a form of a structured fiber, wire, mesh, or membrane.

33. The method of claim 32, wherein the structured composition is incorporated into a catheter, stent, cannula, or like flexible tubular device capable of being delivered locally to a position within the vascular system of a stent.

34. The method of claim 33, wherein the structured composition is alternatively extendible from and retractable into the catheter, stent, cannula, or like flexible tubular device.

35. The method of claim 33, wherein the exterior surface of the catheter, stent, cannula, or like flexible tubular device is coated with the structured composition.

36. The method of claim 29, wherein the linking group comprises one or more internal covalent aliphatic or aromatic amide, amine, ester, ether, thioamide, thioester, or thioether bonds, or a coordinative ligand linkage to a transition metal.

37. The method of claim 29, wherein the DNA is genomic DNA.

38. The method of claim 29, wherein the DNA is linked to the linking group by:
(a) a covalent aliphatic or aromatic amide, amine, ester, ether, thioamide, thioester, or thioether bond; or
(b) intercalation or an electrostatic, pi-pi, and/or hydrogen-bonding mechanisms with a moiety on the linking group; or
(c) bonding to a cis-platin-like moiety covalently attached to the linking group.

39. The method of claim 29, wherein the scaffold and/or the organic polymer surface or hydroxylated inorganic surface comprises the polyhydroxylated organic polymer comprising (co)-polymerized (meth)acrylate linkages.

40. The method of claim 29, wherein the scaffold and/or the organic polymer surface or hydroxylated inorganic surface comprises the lithographically patterned organic polymer.

41. The method of claim 29, wherein the scaffold comprises the three-dimensionally (3D) photopolymerized patterned polymer structure.

42. The method of claim 29, wherein the scaffold and/or the organic polymer surface or hydroxylated inorganic surface comprises the organic polymer and the linking group is covalently bound to the organic polymer surface, the covalent bond resulting from the co-polymerization of an unsaturated moiety of a linker group precursor with a prepolymer of the organic polymer to form the linking group pendant to the surface.

43. The method of claim 29, wherein the linking group is covalently bound to the organic polymer surface comprising the polyhydroxylated organic polymer.

44. The method of claim 29, wherein the linking group is covalently bound to the organic polymer surface by an aliphatic or aromatic amide, amine, ester, ether, thioamide, thioester, thioether, or silyl ether linkage.

45. The method of claim 29, wherein the scaffold and/or the organic polymer surface or hydroxylated inorganic surface comprises the polyhydroxylated organic polymer comprising the (co)polymerized polyvinyl alcohol, polyalkylhydroxy(meth)acrylate, polyhydroxyalkyl(meth)acrylamide, monoglycerol(meth)acrylate, monoglycerol(meth)acrylamide, or combination thereof.

46. The method of claim 45, wherein the polyhydroxylated organic polymer comprises (co)polymerized 2-hydroxyethyl(meth)acrylate, 2-hydroxypropyl(meth)acrylate, 3-hydroxypropyl(meth)acrylate, 2-hydroxybutyl(meth)acrylate, 3-hydroxybutyl(meth)acrylate, and 4-hydroxybutyl (meth)acrylate, and glycerol mono(meth)acrylate.

47. The method of claim 29, wherein the scaffold and/or the organic polymer surface or/or inorganic surface comprises a hydroxylated metal or a hydroxylated metalloid.

48. The method of claim 29, wherein the scaffold and/or the organic polymer surface or the hydroxylated inorganic surface comprises a hydroxylated metal oxide or a hydroxylated metalloid oxide.

49. The method of claim 48, wherein the linking group is covalently bound to the hydroxylated inorganic surface.

50. The method of claim 49, wherein the hydroxylated inorganic surface comprises a hydrous oxide of Al, B, Ca, Cr, Fe, Mg, Ni, Si, Sn, Ti, Zn, or Zr.

51. The method of claim 49, wherein the hydroxylated inorganic surface comprises a hydroxylated silicate glass or clay.

52. The method of claim 49, wherein the linker group is covalently attached to the hydroxylated inorganic surface by a metal silyl ether linkage.

53. The method of claim 29, further comprising a captured drug, wherein the captured drug is bonded or otherwise attached to the DNA.

54. The method of claim 53, wherein the captured drug comprises doxorubicin (DOX), epirubicin (EPI), daunorubicin, a nitrogen mustard, a nitrosourea, an alkyl sulfonate, a triazine, an ethylenimine, trabectedin, or a Pt-drug.

55. The method of claim 29, wherein the structured composition is in physical contact with a physiological fluid.

56. The method of claim 55, wherein the physiological fluid is saline, blood, serum, or blood plasma.

57. The method of claim 29, the method comprising trans- or intra-arterial chemotherapy.

* * * * *